US010293553B2

(12) United States Patent
Racenet et al.

(10) Patent No.: US 10,293,553 B2
(45) Date of Patent: May 21, 2019

(54) BUTTRESS BRACHYTHERAPY AND INTEGRATED STAPLE LINE MARKERS FOR MARGIN IDENTIFICATION

(71) Applicant: Covidien LP, Mansfield, MA (US)

(72) Inventors: David Racenet, Killingworth, CT (US); Gerald Hodgkinson, Guilford, CT (US); William Powers, Cheshire, CT (US)

(73) Assignee: Covidien LP, Mansfield, MA (US)

( * ) Notice: Subject to any disclaimer, the term of this patent is extended or adjusted under 35 U.S.C. 154(b) by 746 days.

(21) Appl. No.: 14/699,502

(22) Filed: Apr. 29, 2015

(65) Prior Publication Data
US 2015/0245835 A1 Sep. 3, 2015

Related U.S. Application Data

(63) Continuation-in-part of application No. 14/163,386, filed on Jan. 24, 2014, now Pat. No. 9,610,080, which
(Continued)

(51) Int. Cl.
A61B 17/068 (2006.01)
B29C 65/00 (2006.01)
(Continued)

(52) U.S. Cl.
CPC ...... B29C 66/727 (2013.01); A61B 17/07292 (2013.01); B29C 65/002 (2013.01);
(Continued)

(58) Field of Classification Search
CPC . B29C 66/727; B29C 65/002; Y10T 156/109; B29L 2031/753;
(Continued)

(56) References Cited

U.S. PATENT DOCUMENTS 3,054,406 A 9/1962 Usher
3,079,606 A 3/1963 Bobrov et al.
(Continued)

FOREIGN PATENT DOCUMENTS

CA 2 667 434 A1 5/2008
DE 19924311 A1 11/2000
(Continued)

OTHER PUBLICATIONS

European Search Report corresponding to EP 05 02 2585.3, completed Jan. 25, 2006 dated Feb. 3, 2006; (4 pp).
(Continued)

Primary Examiner — Robert F Long
Assistant Examiner — Xavier A Madison

(57) ABSTRACT

A surgical buttress for use in a surgical stapling apparatus is provided. The surgical buttress includes an elongate rectangular body portion defining a width; a nose portion integrally formed with and extending from a distal end of the body portion, the nose portion defining a width that is less than the width of the body portion; a neck portion integrally formed with and extending from a distal end of the nose portion, the neck portion defining a width; a head portion integrally formed with and connected to a distal end of the neck portion, the head portion defining a width; and a tail portion integrally formed with and extending from a proximal end of the body portion, the tail portion defining a width that is less that the width of the body portion. The surgical buttress is formed from a material having filaments. The surgical buttress include radioactive material.

22 Claims, 22 Drawing Sheets

Related U.S. Application Data is a continuation-in-part of application No. 13/955,341, filed on Jul. 31, 2013, now Pat. No. 9,693,772, which is a continuation-in-part of application No. 13/419,565, filed on Mar. 14, 2012, now Pat. No. 8,561,873, which is a continuation of application No. 12/579,605, filed on Oct. 15, 2009, now Pat. No. 8,157,151.

(60) Provisional application No. 61/992,520, filed on May 13, 2014, provisional application No. 61/696,906, filed on Sep. 5, 2012.

(51) Int. Cl.
  *A61B 17/072* (2006.01)
  *B29L 31/00* (2006.01)
  *A61B 17/00* (2006.01)
  *A61B 90/00* (2016.01)

(52) U.S. Cl.
  CPC ........... *A61B 2017/00893* (2013.01); *A61B 2090/061* (2016.02); *A61B 2090/0807* (2016.02); *B29L 2031/753* (2013.01); *Y10T 156/109* (2015.01)

(58) Field of Classification Search
  CPC ........ A61B 17/07292; A61B 2090/061; A61B 2090/0807; A61B 2017/00893
  USPC .......................................... 227/175.1–182.1
  See application file for complete search history.

(56) References Cited

U.S. PATENT DOCUMENTS

| | | |
|---|---|---|
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,754,745 A * | 7/1988 | Horowitz ............. A61N 5/1007 600/8 |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,030,195 A * | 7/1991 | Nardi ................... A61N 5/1029 600/7 |
| 5,040,715 A | 8/1991 | Green et al. |
| 5,057,334 A | 10/1991 | Vail |
| 5,065,929 A | 11/1991 | Schulze et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,460,592 A | 10/1995 | Langton et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,906,573 A | 5/1999 | Aretz |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,333 A | 2/2000 | Sioshansi et al. |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,146,322 A | 11/2000 | Papirov et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,264,596 B1 | 7/2001 | Weadock |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,471,630 B1 | 10/2002 | Sioshansi et al. |
| 6,500,777 B1 | 12/2002 | Wiseman et al. |

(56) References Cited

U.S. PATENT DOCUMENTS

| | | | |
|---|---|---|---|
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,547,812 B1 | 4/2003 | Hu |
| 6,551,356 B2 | 4/2003 | Rousseau |
| 6,566,406 B1 | 5/2003 | Pathak et al. |
| 6,575,887 B1 | 6/2003 | Schrayer |
| 6,575,888 B2 | 6/2003 | Zamora et al. |
| 6,589,502 B1 | 7/2003 | Coniglione et al. |
| 6,590,095 B1 | 7/2003 | Schleicher et al. |
| 6,592,597 B2 | 7/2003 | Grant et al. |
| 6,599,230 B2 | 7/2003 | Hastings et al. |
| 6,605,294 B2 | 8/2003 | Sawhney |
| 6,616,592 B1 | 9/2003 | Rosenthal et al. |
| 6,627,749 B1 | 9/2003 | Kumar |
| 6,629,988 B2 | 10/2003 | Weadock |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,679,824 B1 * | 1/2004 | Reed ................ A61N 5/1027 600/7 |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,749,553 B2 | 6/2004 | Brauckman et al. |
| 6,761,680 B2 | 7/2004 | Terwilliger et al. |
| 6,764,720 B2 | 7/2004 | Pui et al. |
| 6,773,390 B2 | 8/2004 | McDaniel |
| 6,773,458 B1 | 8/2004 | Brauker et al. |
| 6,786,858 B2 | 9/2004 | Terwilliger et al. |
| 6,818,018 B1 | 11/2004 | Sawhney |
| 6,820,318 B2 | 11/2004 | Terwilliger et al. |
| 6,896,684 B2 | 5/2005 | Monassevitch et al. |
| 6,926,733 B2 | 8/2005 | Stinson |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 6,969,344 B2 | 11/2005 | Drobnik et al. |
| 6,997,862 B2 | 2/2006 | Terwilliger et al. |
| 7,008,368 B2 | 3/2006 | Terwilliger et al. |
| 7,009,034 B2 | 3/2006 | Pathak et al. |
| 7,060,020 B2 | 6/2006 | Terwilliger et al. |
| 7,060,087 B2 | 6/2006 | DiMatteo et al. |
| 7,070,554 B2 | 7/2006 | White et al. |
| 7,087,065 B2 | 8/2006 | Ulmsten et al. |
| 7,105,018 B1 | 9/2006 | Yip et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,311,720 B2 | 12/2007 | Mueller et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,649,089 B2 | 1/2010 | Kumar et al. |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Criscuolo et al. |
| 7,722,642 B2 | 5/2010 | Williamson, IV et al. |
| 7,744,627 B2 | 6/2010 | Orban, III et al. |
| 7,776,060 B2 | 8/2010 | Mooradian et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,942,931 B2 | 5/2011 | Gonzalez et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,972,260 B2 | 7/2011 | Wazer et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,028,883 B2 | 10/2011 | Stopek |
| 8,033,483 B2 | 10/2011 | Fortier et al. |
| 8,038,045 B2 | 10/2011 | Bettuchi et al. |
| 8,061,520 B2 | 11/2011 | Stopek |
| 8,062,330 B2 | 11/2011 | Prommersberger et al. |
| 8,069,980 B2 | 12/2011 | Stopek et al. |
| 8,083,119 B2 | 12/2011 | Prommersberger |
| 8,123,766 B2 | 2/2012 | Bauman et al. |
| 8,123,767 B2 | 2/2012 | Bauman et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,192,460 B2 | 6/2012 | Orban, III et al. |
| 8,210,414 B2 | 7/2012 | Bettuchi et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,267,849 B2 | 9/2012 | Wazer et al. |
| 8,276,800 B2 | 10/2012 | Bettuchi |
| 8,286,849 B2 | 10/2012 | Bettuchi |
| 8,292,068 B2 | 10/2012 | Stopek et al. |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson et al. |
| 8,348,130 B2 | 1/2013 | Shah et al. |
| 8,365,972 B2 | 2/2013 | Aranyi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,393,514 B2 | 3/2013 | Shelton, IV et al. |

(56) References Cited

U.S. PATENT DOCUMENTS

| | | |
|---|---|---|
| 8,408,440 B2 | 4/2013 | Olson et al. |
| 8,413,871 B2 | 4/2013 | Racenet et al. |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,454,489 B2 | 6/2013 | Drobnik et al. |
| 8,464,925 B2 | 6/2013 | Hull et al. |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,486,047 B2 | 7/2013 | Stopek |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,529,600 B2 | 9/2013 | Woodard, Jr. et al. |
| 8,529,819 B2 | 9/2013 | Ostapoff et al. |
| 8,540,131 B2 | 9/2013 | Swayze |
| 8,551,132 B2 | 10/2013 | Eskridge et al. |
| 8,551,138 B2 | 10/2013 | Orban et al. |
| 8,556,918 B2 | 10/2013 | Bauman et al. |
| 8,561,873 B2 | 10/2013 | Ingmanson et al. |
| 8,579,785 B2 | 11/2013 | Shariati |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,631,989 B2 | 1/2014 | Aranyi et al. |
| 8,668,129 B2 | 3/2014 | Olson |
| 8,684,250 B2 | 4/2014 | Bettuchi et al. |
| 8,757,466 B2 | 6/2014 | Olson et al. |
| 8,789,737 B2 | 7/2014 | Hodgkinson et al. |
| 8,820,606 B2 | 9/2014 | Hodgkinson |
| 8,870,050 B2 | 10/2014 | Hodgkinson |
| 8,939,344 B2 | 1/2015 | Olson et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 2001/0044567 A1* | 11/2001 | Zamora ............. A61K 51/1282 600/3 |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0052622 A1 | 5/2002 | Rousseau |
| 2002/0086990 A1 | 7/2002 | Kumar et al. |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0078209 A1 | 4/2003 | Schmidt |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios et al. |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0131225 A1 | 6/2005 | Kumar et al. |
| 2005/0143756 A1 | 6/2005 | Jankowski |
| 2005/0149073 A1 | 7/2005 | Arani et al. |
| 2005/0154093 A1 | 7/2005 | Kwon et al. |
| 2005/0228446 A1 | 10/2005 | Mooradian et al. |
| 2005/0245965 A1 | 11/2005 | Orban, III et al. |
| 2006/0004407 A1 | 1/2006 | Hiles et al. |
| 2006/0008505 A1 | 1/2006 | Brandon |
| 2006/0085034 A1 | 4/2006 | Bettuchi |
| 2006/0093672 A1 | 5/2006 | Kumar et al. |
| 2006/0121266 A1 | 6/2006 | Fandel et al. |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0054880 A1 | 3/2007 | Saferstein et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0213522 A1 | 9/2007 | Harris et al. |
| 2007/0237741 A1 | 10/2007 | Figuly et al. |
| 2007/0237742 A1 | 10/2007 | Figuly et al. |
| 2007/0243227 A1 | 10/2007 | Gertner |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0164440 A1 | 7/2008 | Maase et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0194805 A1 | 8/2008 | Vignon et al. |
| 2008/0200949 A1 | 8/2008 | Hiles et al. |
| 2008/0214695 A1 | 9/2008 | Pathak et al. |
| 2008/0220047 A1 | 9/2008 | Sawhney et al. |
| 2008/0230583 A1 | 9/2008 | Heinrich |
| 2008/0249398 A1 | 10/2008 | Harder et al. |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |

(56) References Cited

U.S. PATENT DOCUMENTS

| | | |
|---|---|---|
| 2009/0012347 A1 | 1/2009 | Helle et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0220560 A1 | 9/2009 | Wan et al. |
| 2009/0263441 A1 | 10/2009 | McKay |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0065660 A1 | 3/2010 | Hull et al. |
| 2010/0072254 A1 | 3/2010 | Aranyi et al. |
| 2010/0096481 A1 | 4/2010 | Hull et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0203151 A1 | 8/2010 | Hiraoka |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0082427 A1 | 4/2011 | Golzarian et al. |
| 2011/0087279 A1 | 4/2011 | Shah et al. |
| 2011/0089375 A1 | 4/2011 | Chan et al. |
| 2011/0215132 A1 | 9/2011 | Aranyi et al. |
| 2011/0293690 A1 | 12/2011 | Griffin et al. |
| 2012/0074199 A1 | 3/2012 | Olson et al. |
| 2012/0080336 A1 | 4/2012 | Shelton, IV et al. |
| 2012/0125792 A1* | 5/2012 | Cassivi ............ A61B 17/07207 206/205 |
| 2012/0156289 A1 | 6/2012 | Blaskovich et al. |
| 2012/0187179 A1 | 7/2012 | Gleiman |
| 2012/0241498 A1 | 9/2012 | Gonzalez et al. |
| 2012/0241499 A1 | 9/2012 | Baxter, III et al. |
| 2013/0037596 A1 | 2/2013 | Bear et al. |
| 2013/0105548 A1 | 5/2013 | Hodgkinson et al. |
| 2013/0105553 A1 | 5/2013 | (Tarinelli) Racenet et al. |
| 2013/0112732 A1 | 5/2013 | Aranyi et al. |
| 2013/0112733 A1 | 5/2013 | Aranyi et al. |
| 2013/0123816 A1 | 5/2013 | Hodgkinson et al. |
| 2013/0146641 A1 | 6/2013 | Shelton, IV et al. |
| 2013/0153635 A1 | 6/2013 | Hodgkinson |
| 2013/0153636 A1 | 6/2013 | Shelton, IV et al. |
| 2013/0153638 A1 | 6/2013 | Carter et al. |
| 2013/0153639 A1 | 6/2013 | Hodgkinson et al. |
| 2013/0153640 A1 | 6/2013 | Hodgkinson |
| 2013/0153641 A1 | 6/2013 | Shelton, IV et al. |
| 2013/0161374 A1 | 6/2013 | Swayze et al. |
| 2013/0193186 A1 | 8/2013 | (Tarinelli) Racenet et al. |
| 2013/0193192 A1 | 8/2013 | Casasanta, Jr. et al. |
| 2013/0209659 A1 | 8/2013 | Racenet et al. |
| 2013/0240600 A1 | 9/2013 | Bettuchi |
| 2013/0240601 A1 | 9/2013 | Bettuchi et al. |
| 2013/0240602 A1 | 9/2013 | Stopek |
| 2013/0277411 A1 | 10/2013 | Hodgkinson et al. |
| 2013/0306707 A1 | 11/2013 | Viola et al. |
| 2013/0310873 A1 | 11/2013 | Stopek (Nee Prommersberger) et al. |
| 2013/0327807 A1 | 12/2013 | Olson et al. |
| 2014/0012317 A1 | 1/2014 | Orban et al. |
| 2014/0021242 A1 | 1/2014 | Hodgkinson et al. |
| 2014/0027490 A1 | 1/2014 | Marczyk et al. |
| 2014/0034704 A1 | 2/2014 | Ingmanson et al. |
| 2014/0048580 A1 | 2/2014 | Merchant et al. |
| 2014/0061280 A1 | 3/2014 | Ingmanson et al. |
| 2014/0066688 A1* | 3/2014 | Cassivi ............... A61N 5/1007 600/7 |
| 2014/0097224 A1 | 4/2014 | Prior |
| 2014/0131418 A1 | 5/2014 | Kostrzewski |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0155916 A1 | 6/2014 | Hodgkinson et al. |
| 2014/0158742 A1 | 6/2014 | Stopek (Nee Prommersberger) et al. |
| 2014/0166721 A1 | 6/2014 | Stevenson et al. |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson et al. |
| 2014/0252062 A1 | 9/2014 | Mozdzierz |
| 2015/0001276 A1 | 1/2015 | Hodgkinson et al. |
| 2015/0041347 A1 | 2/2015 | Hodgkinson |
| 2015/0097018 A1 | 4/2015 | Hodgkinson |
| 2015/0115015 A1 | 4/2015 | Prescott et al. |

FOREIGN PATENT DOCUMENTS

| | | |
|---|---|---|
| EP | 0 327 022 A2 | 8/1989 |
| EP | 0 594 148 A1 | 4/1994 |
| EP | 0 667 119 A1 | 8/1995 |
| EP | 1 064 883 A1 | 1/2001 |
| EP | 1 256 317 A2 | 11/2002 |
| EP | 1 256 318 A1 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 A1 | 8/2007 |
| EP | 1 929 958 A2 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 A1 | 8/2009 |
| EP | 2 090 244 A2 | 8/2009 |
| EP | 2 090 252 A2 | 8/2009 |
| EP | 2 198 787 A1 | 6/2010 |
| EP | 2 236 098 A2 | 10/2010 |
| EP | 2 236 099 A1 | 10/2010 |
| EP | 2 292 276 A2 | 3/2011 |
| EP | 2 305 135 A1 | 4/2011 |
| EP | 2 311 386 A2 | 4/2011 |
| EP | 2 436 348 A1 | 4/2012 |
| EP | 2 462 880 A2 | 6/2012 |
| EP | 2 481 359 A1 | 8/2012 |
| EP | 2 517 637 A1 | 10/2012 |
| EP | 2 586 380 A1 | 5/2013 |
| EP | 2 604 195 A1 | 6/2013 |
| EP | 2 604 197 A2 | 6/2013 |
| EP | 2 620 105 A1 | 7/2013 |
| EP | 2 620 106 A2 | 7/2013 |
| EP | 2 630 922 A1 | 8/2013 |
| EP | 2 644 125 A2 | 10/2013 |
| EP | 2 762 091 A2 | 8/2014 |
| JP | 07-124166 A | 5/1995 |
| JP | 2000-166933 A | 6/2000 |
| JP | 2002-202213 A | 7/2002 |
| JP | 2007-124166 A | 5/2007 |

(56) References Cited

FOREIGN PATENT DOCUMENTS

| | | |
|---|---|---|
| WO | 90/05489 A1 | 5/1990 |
| WO | 95/16221 A1 | 6/1995 |
| WO | 96/22055 A1 | 7/1996 |
| WO | 97/01989 A1 | 1/1997 |
| WO | 97/13463 A1 | 4/1997 |
| WO | 98/17180 A1 | 4/1998 |
| WO | 99/45849 A1 | 9/1999 |
| WO | 03/082126 A1 | 10/2003 |
| WO | 03/088845 A2 | 10/2003 |
| WO | 03/094743 A1 | 11/2003 |
| WO | 03/105698 A2 | 12/2003 |
| WO | 2005079675 A2 | 9/2005 |
| WO | 2006023578 A2 | 3/2006 |
| WO | 2006044490 A2 | 4/2006 |
| WO | 2006083748 A1 | 8/2006 |
| WO | 2007121579 A1 | 11/2007 |
| WO | 2008057281 A2 | 5/2008 |
| WO | 2008109125 A1 | 9/2008 |
| WO | 2010/028332 A2 | 3/2010 |
| WO | 2010075298 A2 | 7/2010 |
| WO | 2011143183 A2 | 11/2011 |
| WO | 2012044848 A1 | 4/2012 |

OTHER PUBLICATIONS

European Search Report corresponding to EP 06 00 4598, completed Jun. 22, 2006; (2 pp).
European Search Report corresponding to EP 06 01 6962.0, completed Jan. 3, 2007 dated Jan. 11, 2007; (10 pp).
International Search Report corresponding to International Application No. PCT/US2005/036740, completed Feb. 20, 2007 dated Mar. 23, 2007; (8 pp).
International Search Report corresponding to International Application No. PCT/US2007/022713, completed Apr. 21, 2008 dated May 15, 2008; (1 p).
International Search Report corresponding to International Application No. PCT/US2008/002981, completed Jun. 9, 2008 dated Jun. 26, 2008; (2 pp).
European Search Report corresponding to EP 08 25 1779, completed Jul. 14, 2008 dated Jul. 23, 2008; (5 pp).
European Search Report corresponding to EP 08 25 1989.3, completed Mar. 11, 2010 dated Mar. 24, 2010; (6 pp).
European Search Report corresponding to EP 10 25 0639.1, completed Jun. 17, 2010 dated Jun. 28, 2010; (7 pp).
European Search Report corresponding to EP 10 25 0715.9, completed Jun. 30, 2010 dated Jul. 20, 2010; (3 pp).
European Search Report corresponding to EP 05 80 4382.9, completed Oct. 5, 2010 dated Oct. 12, 2010; (3 pp).
European Search Report corresponding to EP 10 25 1437.9, completed Nov. 22, 2010 dated Dec. 16, 2010; (3 pp).
European Search Report corresponding to EP 09 25 2897.5, completed Feb. 7, 2011 dated Feb. 15, 2011; (3 pp).
European Search Report corresponding to EP 10 25 0642.5, completed Mar. 25, 2011 dated Apr. 4, 2011; (4 pp).
European Search Report corresponding to EP 11 18 8309.6, completed Dec. 15, 2011 dated Jan. 12, 2012; (3 pp).
European Search Report corresponding to EP 12 15 2229.6, completed Feb. 23, 2012 dated Mar. 1, 2012; (4 pp).
European Search Report corresponding to EP 12 15 0511.9, completed Apr. 16, 2012 dated Apr. 24, 2012; (7 pp).
European Search Report corresponding to EP 12 15 2541.4, completed Apr. 23, 2012 dated May 3, 2012; (10 pp).
European Search Report corresponding to EP 12 16 5609.4, completed Jul. 5, 2012 dated Jul. 13, 2012; (8 pp).
European Search Report corresponding to EP 12 15 8861.0, completed Jul. 17, 2012 dated Jul. 24, 2012; (9 pp).
European Search Report corresponding to EP 12 16 5878.5, completed Jul. 24, 2012 dated Aug. 6, 2012; (8 pp).
Extended European Search Report corresponding to EP 12 19 1035.0, completed Jan. 11, 2013 dated Jan. 18, 2013; (7 pp).
Extended European Search Report corresponding to EP 12 18 6175.1, completed Jan. 15, 2013 dated Jan. 23, 2013; (7 pp).
Extended European Search Report corresponding to EP 12 19 1114.3, completed Jan. 23, 2013 dated Jan. 31, 2013; (10 pp).
Extended European Search Report corresponding to EP 12 19 2224.9, completed Mar. 14, 2013 dated Mar. 26, 2013; (8 pp).
Extended European Search Report corresponding to EP 12 19 6904.2, completed Mar. 28, 2013 dated Jul. 26, 2013; (8 pp).
Extended European Search Report corresponding to EP 12 19 6911.7, completed Apr. 18, 2013 dated Apr. 24, 2013; (8 pp).
Extended European Search Report corresponding to EP 07 00 5842.5, completed May 13, 2013 dated May 29, 2013; (7 pp).
Extended European Search Report corresponding to EP 12 19 8776.2, completed May 16, 2013 dated May 27, 2013; (8 pp).
Extended European Search Report corresponding to EP 12 19 8749.9, completed May 21, 2013 dated May 31, 2013; (8 pp).
Extended European Search Report corresponding to EP 13 15 6297.7, completed Jun. 4, 2013 dated Jun. 13, 20131; (7 pp).
Extended European Search Report corresponding to EP 13 17 3985.6, completed Aug. 19, 2013 dated Aug. 28, 2013; (6 pp).
Extended European Search Report corresponding to EP 13 17 3986.4, completed Aug. 20, 2013 dated Aug. 29, 2013; (6 pp).
Extended European Search Report corresponding to EP 13 17 7437.4, completed Sep. 11, 2013 dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 dated Sep. 30, 2013; (5 pp).
Extended European Search Report corresponding to EP 13 18 3876.5, completed Oct. 14, 2013 dated Oct. 24, 2013; (5 pp).
Extended European Search Report corresponding to EP 13 17 1856.1, completed Oct. 29, 2013 dated Nov. 7, 2013; (8 pp).
Extended European Search Report corresponding to EP 13 18 0373.6, completed Oct. 31, 2013 dated Nov. 13, 2013; (7 pp).
Extended European Search Report corresponding to EP 13 18 0881.8, completed Nov. 5, 2013 dated Nov. 14, 2013; (6 pp).
Extended European Search Report corresponding to EP 13 17 6895.4, completed Nov. 29, 2013 dated Dec. 12, 2013; (5 pp).
Extended European Search Report corresponding to EP 13 18 2911.1, completed Dec. 2, 2013 dated Dec. 16, 2013; (8 pp).
Extended European Search Report corresponding to EP 10 25 1795.0, completed Dec. 11, 2013 dated Dec. 20, 2013; (6 pp).
Extended European Search Report corresponding to EP 13 18 7911.6, completed Jan. 22, 2014 dated Jan. 31, 2014; (8 pp).
Extended European Search Report corresponding to EP 13 19 2111.6, completed Feb. 13, 2014 dated Feb. 27, 2014; (10 pp).
Extended European Search Report corresponding to EP 13 19 5919.9, completed Feb. 10, 2014 dated Mar. 3, 2014; (7 pp).
Extended European Search Report corresponding to EP 08 72 6500.5, completed Feb. 20, 2014 dated Mar. 3, 2014; (7 pp).
Extended European Search Report corresponding to EP 13 19 5019.8, completed Mar. 14, 2014 dated Mar. 24, 2014; (7 pp).
Extended European Search Report corresponding to EP 13 19 6816.6, completed Mar. 28, 2014 dated Apr. 9, 2014; (9 pp).
Extended European Search Report corresponding to EP 13 19 7958.5, completed Apr. 4, 2014 dated Apr. 15, 2014; (8 pp).
European Office Action corresponding to counterpart Int'l Appln. No. EP 15 16 7341.5 dated May 3, 2017.
Extended European Search Report corresponding to EP 13 19 4995.0, completed Jun. 5, 2014 dated Jun. 16, 2014; (5 pp).
Extended European Search Report corresponding to EP 14 15 7195.0, completed Jun. 5, 2014 dated Jun. 18, 2014; (9 pp).
Extended European Search Report corresponding to EP 14 15 6342.9, completed Jul. 22, 2014 dated Jul. 29, 2014; (8 pp).
Extended European Search Report corresponding to EP 14 16 9739.1, completed Aug. 19, 2014 dated Aug. 29, 2014; (7 pp).
Extended European Search Report corresponding to EP 14 15 7997.9, completed Sep. 9, 2014 dated Sep. 17, 2014; (8 pp).
Extended European Search Report corresponding to EP 14 16 8904.2, completed Sep. 10, 2014 dated Sep. 18, 2014; (8 pp).
Extended European Search Report corresponding to EP 13 19 4995.0, completed Jun. 5, 2014 dated Oct. 13, 2014; (10 pp).

(56) References Cited

OTHER PUBLICATIONS

Extended European Search Report corresponding to EP 13 15 4571.7, completed Oct. 10, 2014 dated Oct. 20, 2014; (8 pp).
Extended European Search Report corresponding to EP 14 18 1125.7, completed Oct. 16, 2014 dated Oct. 24, 2014; (7 pp).
Extended European Search Report corresponding to EP 14 18 1127.3, completed Oct. 16, 2014 dated Nov. 10, 2014; (8 pp).
Extended European Search Report corresponding to EP 14 19 0419.3, completed Mar. 24, 2015 dated Mar. 30, 2015; (6 pp).
Extended European Search Report corresponding to counterpart Int'l Appln. No. EP 15 16 7341.5 dated Dec. 17, 2015.
Partial European Search Report corresponding to counterpart International Application EP 15 16 7341.5 dated Sep. 21, 2015; (6 pp).
European Office Action corresponding to counterpart European Patent Appln. No. EP 15 16 7341.5 dated Jan. 29, 2018.

* cited by examiner

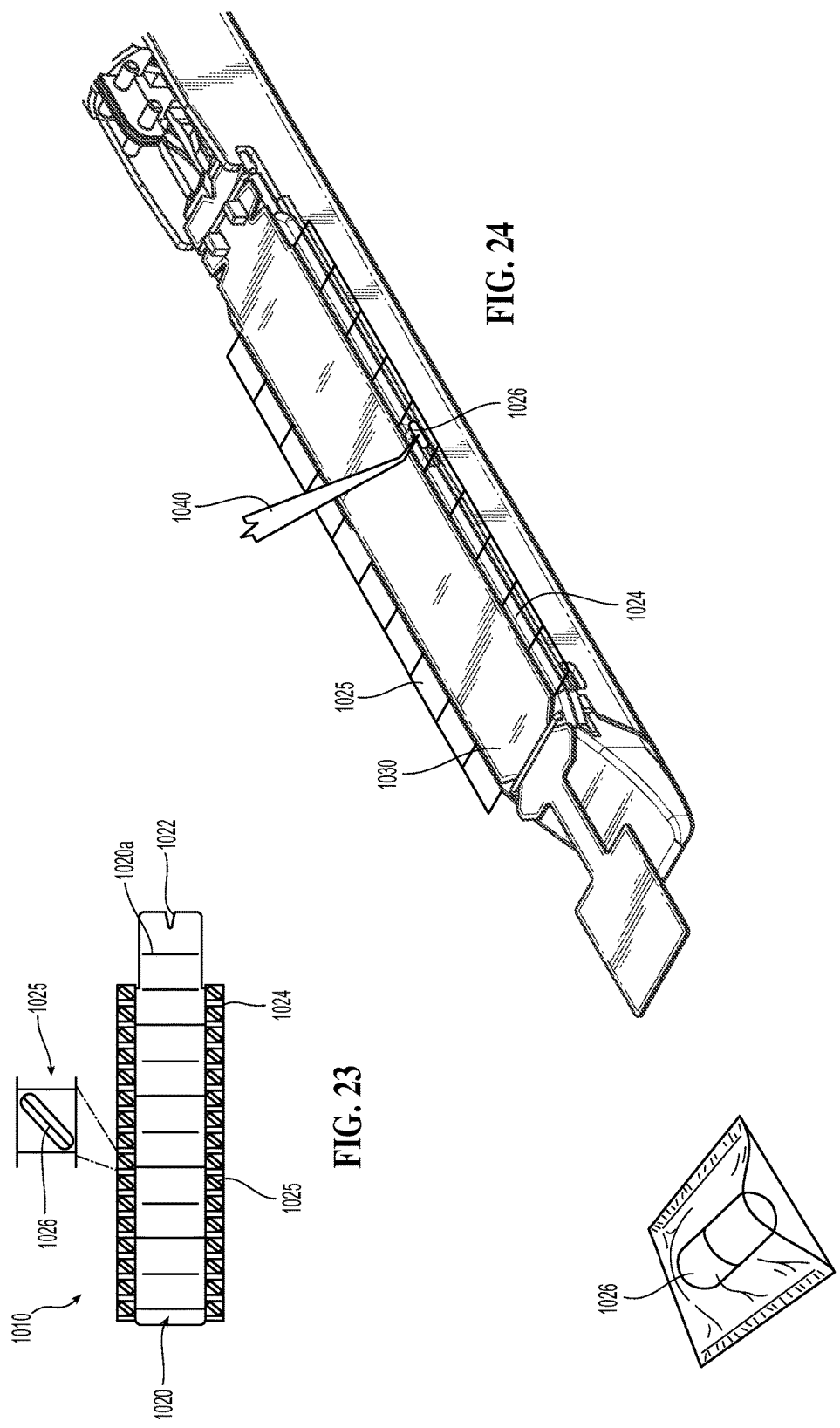

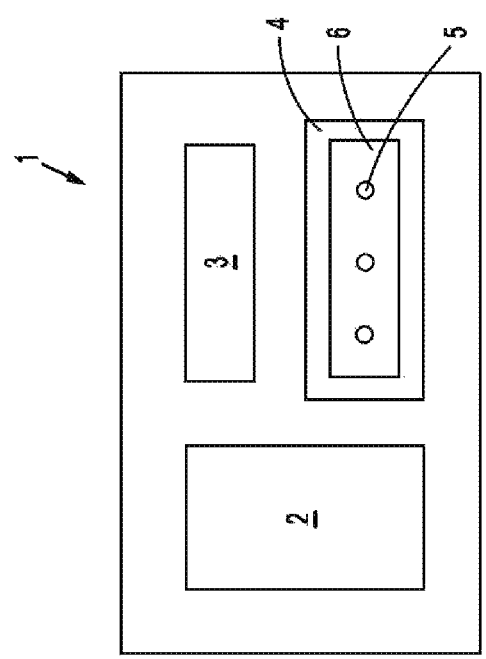

BUTTRESS BRACHYTHERAPY AND INTEGRATED STAPLE LINE MARKERS FOR MARGIN IDENTIFICATION

CROSS-REFERENCE TO RELATED APPLICATIONS

This application claims the benefit of and priority to U.S. Provisional Patent Application No. 61/992,520, filed May 13, 2014, the entire disclosure of which is incorporated by reference herein.

The present application is a Continuation-in-Part Application claiming the benefit of and priority to U.S. patent application Ser. No. 14/163,386, filed on Jan. 24, 2014, which is a Continuation-in-Part Application claiming the benefit of and priority to U.S. patent application Ser. No. 13/955,341, filed on Jul. 31, 2013, which is a Continuation-in-Part Application claiming the benefit of and priority to U.S. patent application Ser. No. 13/419,565, filed on Mar. 14, 2012 (U.S. Pat. No. 8,561,873), which is a Continuation Application claiming the benefit of and priority to U.S. patent application Ser. No. 12/579,605, filed on Oct. 15, 2009 (U.S. Pat. No. 8,157,151), the entire content of each of which is incorporated herein by reference.

U.S. patent application Ser. No. 13/955,341 also claims the benefit of and priority to U.S. Provisional Patent Application No. 61/696,906, filed Sep. 5, 2012, the entire disclosure of which is incorporated by reference herein.

BACKGROUND

1. Technical Field

The present disclosure relates to a surgical stapling apparatus and, more particularly, to a surgical stapling apparatus including a detachable surgical buttress for an anvil and a staple cartridge.

2. Background of Related Art

Surgical stapling instruments that are used to sequentially or simultaneously apply one or more rows of fasteners to join segments of body tissues are well known in the art. The fasteners are typically in the form of surgical staples but two part polymeric fasteners can also be utilized. Such devices generally include a pair of jaws to clamp therebetween the body tissues to be joined. Typically, one of the jaw members includes a staple cartridge which accommodates a plurality of staples arranged in at least two lateral rows while the other jaw member has an anvil that defines a surface for forming the staple legs as the staples are driven from the staple cartridge.

When the stapling instrument is actuated, longitudinally translating cams contact staple drive members in one of the jaws which in turn acts upon staple pushers to sequentially or simultaneously eject the staples from the staple cartridge. A blade can travel between the staple rows to longitudinally cut and/or open the stapled tissue between the rows of staples. Such instruments are disclosed, for example, in U.S. Pat. Nos. 3,079,606 and 3,490,675.

When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible fabric reinforcing material, or a "buttress," between the staple and the underlying tissue. In this method, a layer of buttress material is placed against the tissue and the tissue is stapled in conventional manner. In more recent methods, the layer of buttress is positioned on the stapling instrument itself prior to stapling the tissue. Some surgical staplers utilize fasteners or clips to temporarily connect buttress material to each of the jaws of the staplers, i.e., one disposed on the staple cartridge assembly and the other on the anvil assembly.

WO 2008/109125 discloses a surgical stapling apparatus that includes a cartridge assembly, an anvil assembly, and a surgical buttress releasably secured by an anchor. The anchor releases the surgical buttress during firing of the stapling apparatus.

It is a desire of the present application to provide surgical stapling apparatus with a surgical buttress secured thereto in a manner that minimizes shifting of the surgical buttress, and tearing or other damage to the surgical buttress during assembly. It would also be desirable to provide a single profile buttress that can be used on a surgical staple cartridge assembly and/or a surgical anvil cartridge assembly, as well as cartridge and anvil assemblies of different sizes. Accordingly, it is an object of this disclosure to meet the aforementioned desires.

SUMMARY

The present disclosure relates to a surgical stapling apparatus including a surgical buttress.

According to an aspect of the present disclosure, a surgical stapling apparatus is provided and includes a cartridge assembly defining a first tissue contacting surface, the cartridge assembly housing a plurality of surgical fasteners therein, the cartridge assembly defining at least one distal attachment point and at least one proximal attachment point; an anvil assembly defining a second tissue contacting surface, the anvil assembly movably secured in relation to cartridge assembly, the anvil assembly defining at least one distal attachment point and at least one proximal attachment point, wherein the at least one proximal attachment point of the anvil assembly is offset an axial distance from the at least one proximal attachment point of the cartridge assembly; and a surgical buttress releasably secured to each of the first tissue contacting surface and the second tissue contacting surface, the surgical buttress including a body portion configured to substantially overlie at least one of the first and second tissue contacting surfaces of either the first length and second length cartridge assembly and anvil assembly.

Each surgical buttress defines a distal attachment feature for registration with the distal attachment point of the cartridge assembly and the anvil assembly; and a first proximal attachment feature and a second proximal attachment feature offset an axial distance from the first proximal attachment feature. The first proximal attachment feature registers with the proximal attachment point of the cartridge assembly; and the second proximal attachment feature registers with the proximal attachment point of the anvil assembly.

The surgical buttress may be disposed against the tissue contact surface of the cartridge assembly and the surgical buttress may be disposed against the tissue contact surface of the anvil assembly have substantially the same length.

Each surgical buttress may have the same configuration. Each surgical buttress may be fabricated from a biocompatible and bioabsorbable material.

The surgical stapling apparatus may further include sutures retaining surgical buttresses against the tissue contacting surface of the cartridge assembly and the anvil assembly.

The surgical stapling apparatus may further include a suture retaining a distal end portion of the surgical buttress against a respective one of the cartridge assembly and the anvil assembly, wherein the suture maintains the distal attachment feature of the surgical buttress in registration with the distal attachment point of the respective one of the cartridge assembly and the anvil assembly.

The surgical stapling apparatus may further include a suture retaining a proximal end portion of the surgical buttress against a respective one of the cartridge assembly and the anvil assembly, wherein a suture maintains the first proximal attachment feature of the surgical buttress in registration with the proximal attachment point of the cartridge assembly and the anvil assembly, and wherein a suture maintains the second proximal attachment feature of the surgical buttress in registration with the proximal attachment point of the anvil assembly.

According to another aspect of the present disclosure, a surgical stapling apparatus is provided and includes a cartridge assembly defining a first tissue contacting surface, the cartridge assembly housing a plurality of surgical fasteners therein, the cartridge assembly being either a first length or a second length longer than the first length; an anvil assembly defining a second tissue contacting surface, the anvil assembly movably secured in relation to cartridge assembly, the anvil assembly being either the first length or the second length each corresponding to the length of the cartridge assembly; and a surgical buttress releasably secured to at least one of the first tissue contacting surface and the second tissue contacting surface, the surgical buttress including a head portion, a neck portion, and a body portion. The head portion is connected to a distal end of the body portion by the neck portion. The surgical buttress is configured to substantially overlie at least one of the first and second tissue contacting surfaces of either the first length and second length cartridge assembly and anvil assembly.

The body portion of the surgical buttress may define a recess formed in a proximal edge thereof, the recess longitudinally bisecting the proximal edge. The recess may be a notch having a v-shape profile.

The body portion of the surgical buttress may define at least one pair of opposing proximal recesses, and each of the at least one pair of opposing proximal recesses may be formed on an opposing lateral side of the body portion near a proximal edge of the surgical buttress. The at least one pair of opposing proximal recesses may be a notch having a v-shape profile.

The body portion of the surgical buttress may further define a pair of opposing distal recesses, and each of the pair of opposing distal recesses may be formed on an opposing lateral side of the body portion near a distal edge of the body portion.

The pair of opposing distal recesses may be longitudinally tapered. A distal edge of the body portion of the surgical buttress may be arcuate. A distal edge of the body portion of the surgical buttress may have a transverse width dimension that is less than that of the rest of the body portion. The head portion may have a substantially rectangular shape.

Each surgical buttress may be fabricated from a biocompatible and bioabsorbable material.

According to a further aspect of the present disclosure, a surgical buttress for use in a surgical stapling apparatus is provided. The surgical buttress includes a body portion; a neck portion; and a head portion connected to a distal end of the body portion by the neck portion, wherein the body portion defines at least one pair of opposing proximal recesses, each of the at least one pair of opposing proximal recesses is formed on an opposing lateral side of the body portion near a proximal edge of the body portion.

Each of the at least one pair of opposing proximal recesses may be a notch having a v-shape profile. The body portion may further define a pair of opposing distal recesses, each of the pair of opposing distal recesses may be formed on an opposing lateral side of the body portion near a distal edge of the body portion.

The body portion of the surgical buttress may further define a proximal edge recess formed in a proximal edge thereof, the proximal edge recess longitudinally bisecting the proximal edge. A distal edge of the body portion of the surgical buttress may be arcuate. A distal edge of the body portion of the surgical buttress may have a transverse width dimension less than that of the rest of the body portion. The head portion may have a substantially rectangular shape.

The surgical buttress may be fabricated from a biocompatible and bioabsorbable material.

According to still another aspect of the present disclosure, a surgical buttress is provided for use with a surgical stapling apparatus having a cartridge assembly of any number of lengths and an anvil assembly of any number of lengths corresponding to the lengths of the cartridge assembly, wherein each of the cartridge assembly and anvil assembly defines respective juxtaposed tissue contacting surfaces, and wherein the cartridge assembly includes a plurality of staples stored in staple slots thereof for formation against staple formation pockets of the anvil assembly. The surgical buttress includes a body portion configured and dimensioned to overlie all of the staple slots of the cartridge assembly for any length cartridge assembly, and/or overlie all of the staple formation pockets of the anvil assembly for any length anvil assembly. The surgical buttress further includes a neck portion extending from the body portion; and a head portion connected to the neck portion and opposite a distal end of the body portion, wherein the body portion defines at least one pair of opposing proximal recesses, each of the at least one pair of opposing proximal recesses is formed on an opposing lateral side of the body portion near a proximal edge of the body portion.

According to yet another aspect of the present disclosure a surgical buttress for use in a surgical stapling apparatus is provided and includes an elongate rectangular body portion defining a width; a neck portion integrally formed with and extending from a distal end of the body portion, the neck portion defining a width; a head portion integrally formed with and connected to a distal end of the neck portion, the head portion defining a width; and a tail portion integrally formed with and extending from a proximal end of the body portion, the tail portion defining a width. The width of the tail portion is less than the width of the body portion, and the surgical buttress is formed from a material having filaments.

In certain embodiments, the width of the neck portion is less than the width of the body portion, or the width of the neck portion is less than the width of the tail portion, or the width of the neck portion is more than one-half the width of the body portion.

A length of the head portion may be greater than a length of the tail portion. A length of the head portion may be greater than a length of the neck portion.

The tail portion can define at least one pair of opposing proximal recesses, each of the at least one pair of opposing proximal recesses is formed on an opposing lateral side of the tail portion.

The body portion can further define a pair of opposing distal recesses, each of the pair of opposing distal recesses is formed on an opposing lateral side of the body portion near a distal edge of the body portion.

The tail portion of the surgical buttress can define a proximal edge recess formed in a proximal edge thereof, wherein the proximal edge recess longitudinally bisects the proximal edge.

The surgical buttress is desirably fabricated from a biocompatible and bioabsorbable material.

The surgical buttress can be fabricated from a material selected from the group consisting of polyglycolic acid, glycolide trimethylene carbonate, polyglycolic acid trimethylene carbonate, and blends thereof. The surgical buttress can be formed as a non-woven material.

According to a further aspect of the present disclosure, a surgical buttress is provided for use with a surgical stapling apparatus having a cartridge assembly of any number of lengths and an anvil assembly of any number of lengths corresponding to the lengths of the cartridge assembly, wherein each of the cartridge assembly and anvil assembly defines respective juxtaposed tissue contacting surfaces, and wherein the cartridge assembly includes a plurality of staples stored in staple slots thereof for formation against staple formation pockets of the anvil assembly. The surgical buttress includes an elongate rectangular body portion defining a length and a width; a neck portion integrally formed with and extending from a distal end of the body portion, the neck portion defining a length and a width; a head portion integrally formed with and connected to a distal end of the neck portion, the head portion defining a length and a width; and a tail portion integrally formed with and extending from a proximal end of the body portion, the tail portion defining a length and a width. The width of the tail portion is less than the width of the body portion. The body portion and the tail portion are configured and dimensioned to overlie all of the staple slots of the cartridge assembly for any length cartridge assembly, and/or overlie all of the staple formation pockets of the anvil assembly for any length anvil assembly.

The width of the neck portion may be less than the width of the body portion. The width of the neck portion may be less than the width of the tail portion. The width of the neck portion may be more than one-half the width of the body portion.

The length of the head portion may be greater than the length of the tail portion. The length of the head portion may be greater than the length of the neck portion.

The tail portion may define at least one pair of opposing proximal recesses. Each of the at least one pair of opposing proximal recesses may be formed on an opposing lateral side of the tail portion.

The body portion may further define a pair of opposing distal recesses. Each of the pair of opposing distal recesses may be formed on an opposing lateral side of the body portion near a distal edge of the body portion.

The tail portion of the surgical buttress may define a proximal edge recess formed in a proximal edge thereof. The proximal edge recess may longitudinally bisect the proximal edge.

The surgical buttress may be fabricated from a biocompatible and bioabsorbable material. The surgical buttress may be fabricated from a material selected from the group consisting of polyglycolic acid, glycolide trimethylene carbonate, polyglycolic acid trimethylene carbonate, and blends thereof. The surgical buttress can be made as a non-woven material.

According to another aspect of the present disclosure, a surgical buttress for use in a surgical stapling apparatus is provided. The surgical buttress includes an elongate rectangular body portion defining a width; a nose portion integrally formed with and extending from a distal end of the body portion, the nose portion defining a width that is less than the width of the body portion; a neck portion integrally formed with and extending from a distal end of the nose portion, the neck portion defining a width; a head portion integrally formed with and connected to a distal end of the neck portion, the head portion defining a width; and a tail portion integrally formed with and extending from a proximal end of the body portion, the tail portion defining a width that is less than the width of the body portion. The surgical buttress is formed from a material having filaments.

The width of the neck portion may be less than the width of the nose portion. The width of the neck portion may be less than the width of the tail portion. The width of the neck portion may be more than one-half the width of the body portion.

The tail portion may define at least one pair of opposing proximal recesses, each of the at least one pair of opposing proximal recesses is formed in an opposing lateral side of the tail portion.

The at least one pair of opposing proximal recesses may include a first pair of opposing proximal recesses; and a second pair of opposing proximal recesses, wherein the first pair of opposing proximal recesses is disposed proximal of the second pair of opposing proximal recesses.

Each of the second pair of opposing proximal recesses may extend towards a longitudinal axis of the buttress a greater amount than each of the first pair of opposing proximal recesses.

A side edge of the tail portion, disposed between the first pair of opposing proximal recesses and the second pair of opposing proximal recesses, may taper towards a longitudinal axis of the buttress from a proximal end to a distal end.

Each of the first pair of opposing proximal recesses and each of the second pair of opposing proximal recesses may have a v-shaped profile. A distal edge of each of the first pair of opposing proximal recesses and each of the second pair of opposing proximal recesses may be oriented orthogonal to a longitudinal axis of the buttress.

The body portion may further define a pair of opposing distal recesses. Each of the pair of opposing distal recesses may be formed in opposing lateral sides of the nose portion.

The tail portion of the surgical buttress may define a proximal edge recess formed in a proximal edge thereof, wherein the proximal edge recess may longitudinally bisect the proximal edge.

The surgical buttress may be fabricated from a biocompatible and bioabsorbable material. The surgical buttress may be fabricated from a material selected from the group consisting of polyglycolic acid, glycolide trimethylene carbonate, polyglycolic acid trimethylene carbonate, and blends thereof. The surgical buttress may be formed as a non-woven material.

According to still another aspect of the present disclosure, a surgical buttress for use with a surgical stapling apparatus is provided. The surgical stapling apparatus includes a cartridge assembly of any number of lengths and an anvil assembly of any number of lengths corresponding to the lengths of the cartridge assembly, wherein each of the cartridge assembly and anvil assembly defines respective juxtaposed tissue contacting surfaces, and wherein the cartridge assembly includes a plurality of staples stored in staple slots thereof for formation against staple formation pockets of the anvil assembly.

The surgical buttress includes an elongate rectangular body portion defining a width; a nose portion integrally formed with and extending from a distal end of the body portion, the nose portion defining a width that is less than the width of the body portion; a neck portion integrally formed with and extending from a distal end of the body portion, the neck portion defining a width; a head portion integrally formed with and connected to a distal end of the neck portion, the head portion defining a width; and a tail portion integrally formed with and extending from a proximal end of the body portion, the tail portion defining a width that is less than the width of the body portion.

The body portion and the tail portion are configured and dimensioned to at least one of overlie all of the staple slots of the cartridge assembly for any length cartridge assembly, and overlie all of the staple formation pockets of the anvil assembly for any length anvil assembly.

The width of the neck portion may be less than the width of the nose portion.

The tail portion may define at least one pair of opposing proximal recesses. Each of the at least one pair of opposing proximal recesses may be formed in an opposing lateral side of the tail portion.

The at least one pair of opposing proximal recesses may include a first pair of opposing proximal recesses; and a second pair of opposing proximal recesses, wherein the first pair of opposing proximal recesses is disposed proximal of the second pair of opposing proximal recesses.

Each of the second pair of opposing proximal recesses may extend towards a longitudinal axis of the buttress a greater amount than each of the first pair of opposing proximal recesses.

A side edge of the tail portion, disposed between the first pair of opposing proximal recesses and the second pair of opposing proximal recesses, may taper towards a longitudinal axis of the buttress from a proximal end to a distal end.

Each of the first pair of opposing proximal recesses and each of the second pair of opposing proximal recesses may have a v-shaped profile. A distal edge of each of the first pair of opposing proximal recesses and each of the second pair of opposing proximal recesses may be oriented orthogonal to a longitudinal axis of the buttress.

The body portion may further define a pair of opposing distal recesses. Each of the pair of opposing distal recesses may be formed in opposing lateral sides of the nose portion.

The tail portion of the surgical buttress may define a proximal edge recess formed in a proximal edge thereof, wherein the proximal edge recess longitudinally bisects the proximal edge.

The surgical buttress may be formed from a non-woven material.

According to another aspect of the present disclosure, a surgical buttress for use in a surgical stapling apparatus is provided. The surgical buttress includes an elongate rectangular body portion defining a width and being fabricated from at least one of a biocompatible or bioabsorbable material. The surgical buttress is formed with at least one marking provided at least one of in or on the body portion.

The at least one marking may be formed as a notch.

The at least one marking may include biocompatible and bioabsorbable materials.

The at least one marking may include a biocompatible ink.

The at least one marking may be sewn into the surgical buttress.

The body portion may define at least one pair of notch markings on opposing lateral sides of the surgical buttress.

The body portion may include a plurality of markings. The plurality of markings may be formed by physical notches and ink. The plurality of markings may vary in length. The plurality of markings may be evenly spaced along a length of the surgical buttress.

The surgical buttress may further include a radioactive material embedded within the body portion. The radioactive material may be at least one brachytherapy seed.

The body portion may include a plurality of pores or pockets. The at least one pore may contain a brachytherapy seed.

According to still another aspect of the present disclosure, a surgical buttress for use in a surgical stapling apparatus is provided. The surgical buttress includes a body portion; and radioactive material provided at least one of in or on the body portion.

The body portion may include biocompatible and bioabsorbable materials.

The radioactive material may be at least one brachytherapy seed.

The body portion may include a plurality of pores. At least one pore may contain a brachytherapy seed.

The surgical buttress may be formed with at least one marking provided at least one of in or on the body portion.

According to still another aspect of the present disclosure, a method of embedding radioactive material into a surgical buttress is provided. The method includes providing a surgical buttress; providing a template capable of holding the radioactive material; inserting the radioactive material into the template; mating the template to the surgical buttress; and embedding the radioactive material into the surgical buttress.

The method may further include providing a surgical buttress comprising a plurality of pores or pockets.

The method may further include providing a template that is capable of receiving at least one brachytherapy seed.

The method may further include inserting brachytherapy seeds.

The method may further include embedding the radioactive material into at least 10% of a surface area of the buttress.

The method may further include embedding the radioactive material into a distal end of the surgical buttress.

The method may further include embedding the radioactive material into a proximal end of the surgical buttress.

The method may further include embedding the radioactive material uniformly across a surface area of the surgical buttress.

BRIEF DESCRIPTION OF THE DRAWINGS

The present disclosure will be further described with reference to the accompanying drawings, wherein like reference numerals refer to like parts in the several views, and wherein:

FIG. 23 is a top plan view of a surgical buttress according to certain embodiments of the present disclosure;

FIG. 24 is a perspective view of a staple cartridge assembly having a surgical buttress attached thereto in accordance with embodiments of the present disclosure; and FIG. 25 is a perspective detail view of one of the pockets of a surgical buttress according to certain embodiments of the present disclosure.

FIG. 26 is a schematic illustration of a surgical kit in accordance with an embodiment of the present disclosure.

DETAILED DESCRIPTION OF EMBODIMENTS

Figure 1:
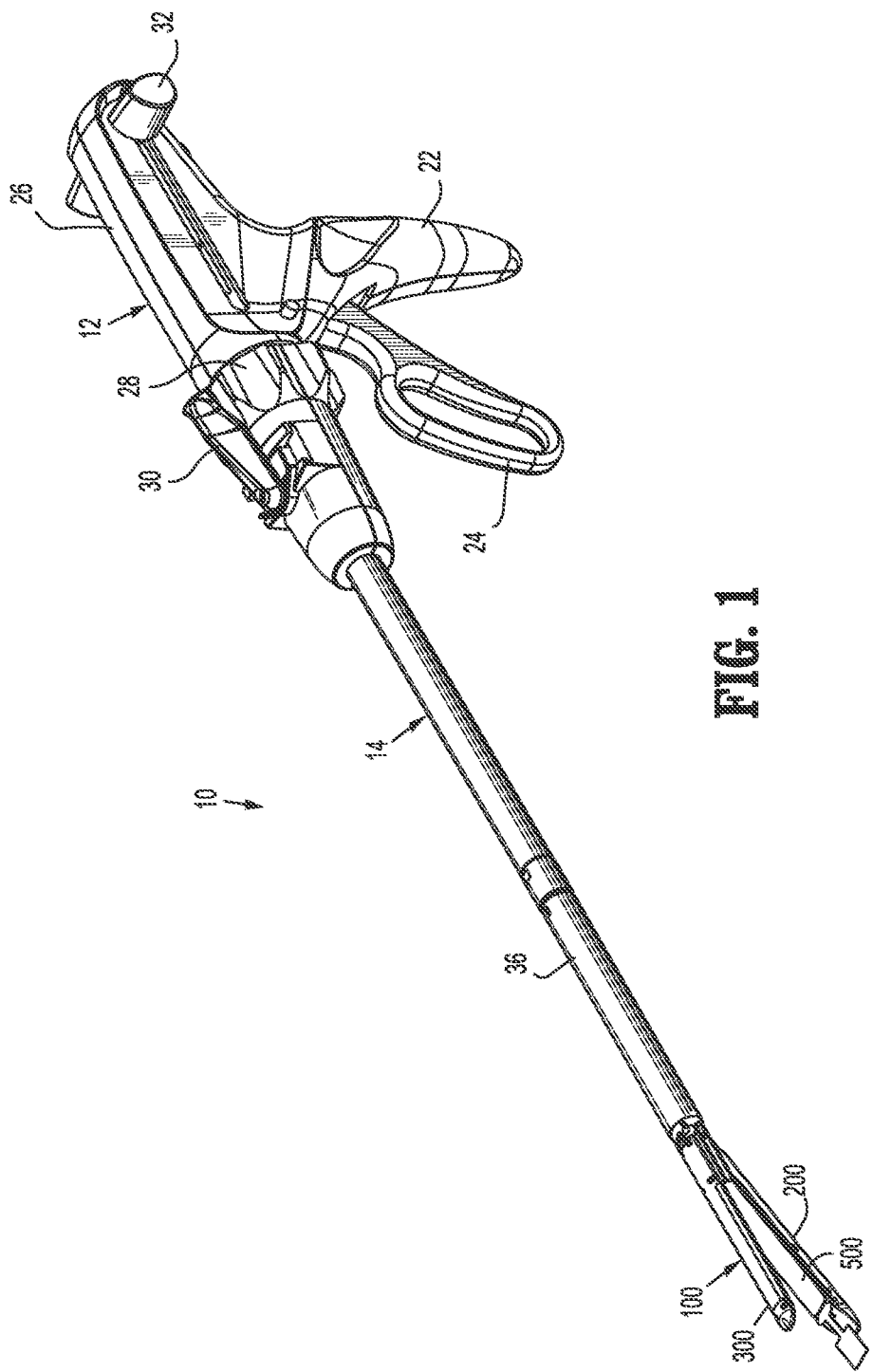
FIG. 1 is a perspective view of a surgical stapling apparatus according to an embodiment of the present disclosure.

Embodiments of the presently disclosed staple line reinforcement for anvil and cartridge of a loading unit of a surgical stapling apparatus will now be described in detail with reference to the drawings, in which like reference numerals designate identical or corresponding elements in each of the several views. In the drawings and in the description that follows, the term "proximal," as is traditional, will refer to the end of the stapling apparatus which is closest to the operator, while the term "distal" will refer to the end of the apparatus which is farthest from the operator.

Referring now to FIG. 1, there is disclosed a linear surgical stapling apparatus, generally referred to as 10. In the interest of brevity, this disclosure will focus primarily on a buttress utilized in a loading unit 100, e.g., a single use loading unit ("SULU") or a disposable loading unit ("DLU"). For simplicity, hereinafter, SULU or DLU will be referred to as "DLU," but it should be understood to include either or both a DLU or SULU. An exemplary example of this type of surgical stapling instrument is disclosed in U.S. Pat. No. 7,128,253, the entire disclosure of which is hereby incorporated by reference herein.

Surgical stapling apparatus 10 generally includes a handle assembly 12 and an elongate body 14 extending distally from handle assembly 12. A DLU 100 is releasably secured to the distal end of elongate body 14. DLU 100 includes a cartridge assembly 200 housing a plurality of surgical fasteners or staples 223 (see FIG. 2) and an anvil assembly 300 movably secured in relation to cartridge assembly 200. Handle assembly 12 includes a stationary handle member 22, a movable handle member 24, and a barrel portion 26. An articulation lever 30 is mounted on the forward end of barrel portion 26 adjacent rotatable member 28 to facilitate articulation of DLU 100. A pair of knobs 32 is movably positioned along barrel portion 26. Knobs 32 are advanced distally to approximate or close cartridge and/or anvil assembly 200, 300, and retracted proximally to unapproximate or open cartridge and/or anvil assembly 200, 300. Actuation of movable handle member 24 applies lines of staples 223 to tissue. In order to properly orient cartridge and anvil assembly 200, 300 relative to the tissue to be stapled, surgical stapling apparatus 10 is additionally provided with a rotatable member 28 on the forward end of barrel portion 26. Rotation of rotatable member 28 relative to handle assembly 12 rotates elongate body 14 and loading unit 100 relative to handle assembly 12 so as to properly orient cartridge assembly 200 and anvil assembly 300 relative to the tissue to be stapled.

Figure 2:
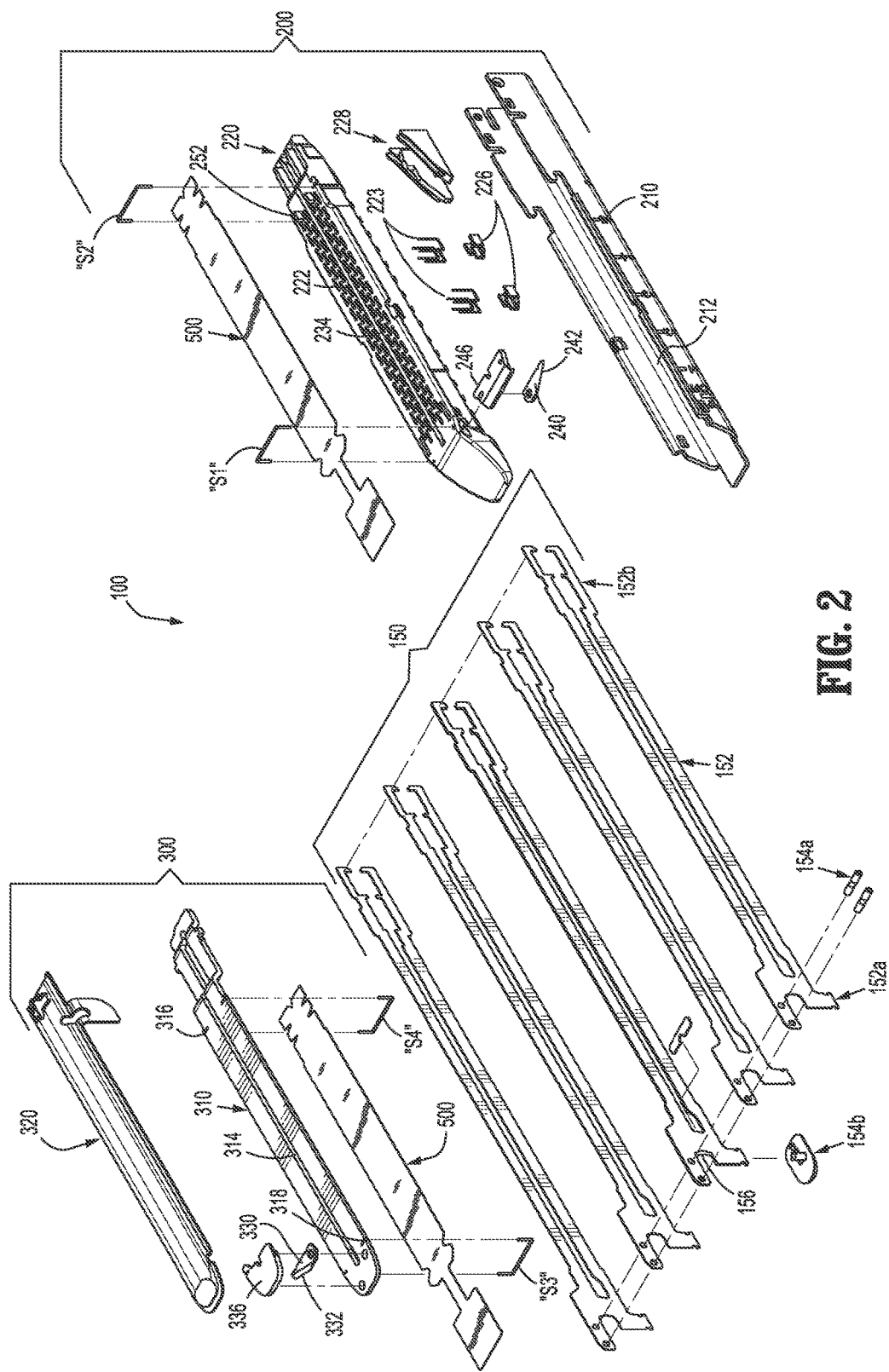
FIG. 2 is a top, exploded, perspective view of a distal end of a DLU of the surgical stapling apparatus of FIG. 1.

As seen in FIG. 2, cartridge assembly 200 includes a carrier 210 defining an elongated support channel 212. Elongated support channel 212 of carrier 210 is dimensioned and configured to selectively receive a staple cartridge 220 therein. Staple cartridge 220 includes retention slots 222 formed therein for receiving a plurality of fasteners 223 and pushers 226. A plurality of spaced apart longitudinal slots extend through staple cartridge 220 to accommodate upstanding cam wedges of actuation sled 228. A central longitudinal slot 234 is formed in and extends along the length of staple cartridge 220 to facilitate passage of knife blade 156 of drive bar 150 therethrough. During operation of surgical stapler 10, actuation sled 228 translates through staple cartridge 220 to advance the cam wedges into sequential contact with pushers 226, to cause pushers 226 to translate vertically within retention slots 222 and urge staples 223 from slots 222 into staple forming cavities of anvil plate 310 of anvil assembly 300.

Figure 10:
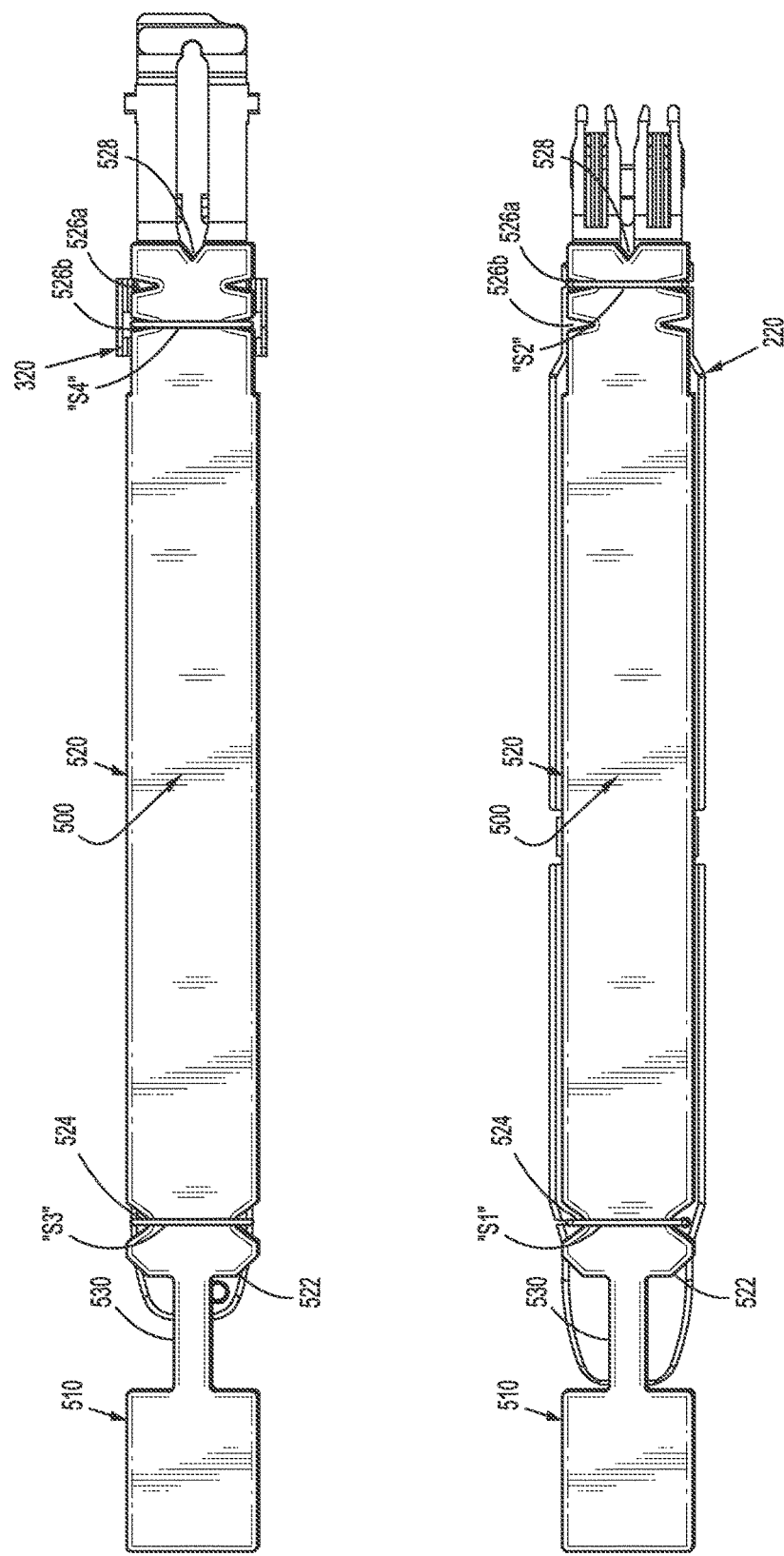
FIG. 10 is a plan view of the cartridge assembly of the DLU of FIGS. 4-8 and the anvil assembly of the DLU of FIG. 9, illustrating the attachment of the buttress of FIG. 3 at different attachment points of a respective cartridge assembly and anvil assembly.

As seen in FIG. 2, cartridge assembly 200 includes a surgical cartridge buttress 500 operatively secured to an upper surface of staple cartridge 220, by sutures "S1, S2," to overlie at least some of retention slots 222 and/or at least a portion of a length of longitudinal slot 234. A first suture "S1" is threaded through each of a distal pair of recesses or attachment points 238 and around/over distal portion of cartridge buttress 500 and, and a second suture "S2" is threaded through each of a proximal pair of recesses or attachment points 236 and around/over proximal portion of cartridge buttress 500. A first end of each suture "S1, S2" may be anchored or fixed in a respective one recesses of the proximal and distal pair of recesses or attachment points 236, 238 while a second end of each suture "S1, S2" passes transversely across respective distal and proximal portions of cartridge buttress 500 and is anchored or fixed in a respective other recess of the proximal and distal pair of recesses or attachment points 236, 238. As seen in FIG. 10, cartridge assembly 200 defines an axial distance "D1" between the distal pair of recesses or attachment points 238 and the proximal pair of recesses or attachment points 236.

Figure 9:
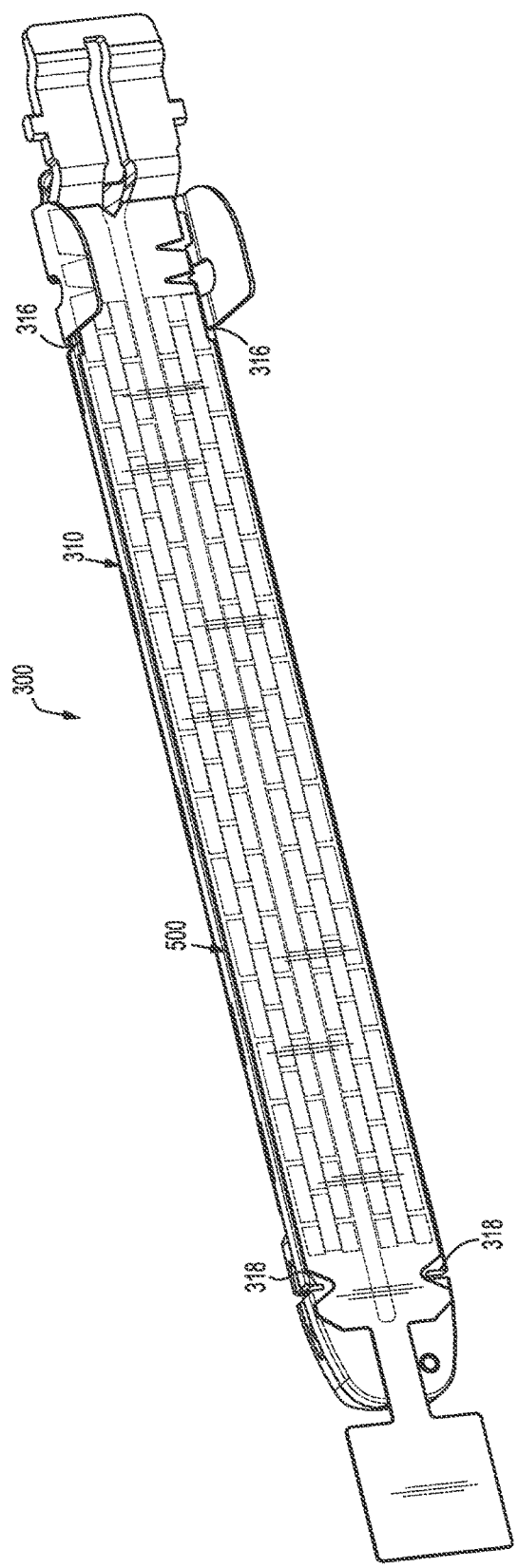
FIG. 9 is a perspective view of an anvil assembly of the DLU of FIG. 2, illustrating the buttress of FIG. 3 secured thereto.

With reference still to FIG. 2, anvil assembly 300 includes an anvil plate 310 having a plurality of staple deforming pockets/cavities 310a (see FIG. 9) and a cover plate 320 secured to a top surface of anvil plate 310. Anvil assembly 300 further includes a knife blade 330 operatively interposed within the cavity defined between anvil plate 310 and cover plate 320.

Anvil plate 310 defines a proximal pair of recesses or attachment points 316 formed near a proximal end of anvil plate 310 and disposed, one each, on opposed sides of longitudinal slot 314. Anvil plate 310 defines a distal pair of recesses or attachment points 318 formed near a distal end of anvil plate 310 and disposed, one each, on opposed sides of longitudinal slot 314. At least one recess of each of the proximal pair of recesses or attachment points 316 and the distal pair of recesses or attachment points 318 is in the form of a slot or notch having a constricting profile so as to frictionally engage and/or pinch a suture "S". Anvil assembly 300 further includes a surgical anvil buttress 500 operatively secured to a lower surface of anvil plate 310, by sutures "S3, S4," to overlie at least some of anvil pockets 310a and/or at least a portion of a length of longitudinal slot 314.

With reference still to FIG. 2, anvil buttress 500 is secured to a lower surface of anvil plate 310, by anchors "S3, S4", to overlie at least some of the anvil pockets and/or at least a portion of a length of longitudinal slot 314. In particular, an anchor "S3" is threaded across a distal portion of the anvil buttress 500 and each of the corresponding distal pair of recesses or attachment points 318, and an anchor "S4" is threaded across a proximal portion of anvil buttress 500 and each of the corresponding proximal pair of recesses or attachment points 316. As seen in FIG. 10, anvil assembly 300 defines an axial distance "D2" between the distal pair of recesses or attachment points 318 and the proximal pair of recesses or attachment points 316.

Reference may be made to U.S. patent application Ser. No. 12/342,400, filed on Dec. 23, 2008 (U.S. Pat. No. 8,011,555), the entire content of which is hereby incorporated herein by reference, for a detailed discussion of the construction and operation of surgical stapling apparatus 10, cartridge assembly 200 and/or anvil assembly 300.

It is contemplated that the cartridge buttress and/or anvil buttress can be attached by other means. For example, in any of the embodiments disclosed herein, the buttresses can be attached using adhesives, welding, and/or attachment features incorporated in the buttress material.

Buttress 500 for each of cartridge assembly 200 and anvil assembly 300 is provided to reinforce and seal staple lines applied to tissue by surgical stapling apparatus 10. Cartridge assembly 200 and anvil assembly 300 are particularly configured to allow surgical buttresses 500 to be localized on inwardly facing surfaces of cartridge assembly 200 and anvil assembly 300 in order to facilitate passage of surgical stapling apparatus 10 into the body of a patient without risk of tearing or wrinkling of the respective buttresses as surgical stapling apparatus 10 is inserted into and manipulated within the body of a patient. The material from which the buttress 500 is formed may be bioabsorbable or non-bioabsorbable. It should be understood that any combination of natural, synthetic, bioabsorbable and non-bioabsorbable materials may be used to form the buttress material. The buttress material may be porous or non-porous or a combination of porous and non-porous layers. The non-porous buttress material may be utilized to retard or prevent tissue ingrowth from surrounding tissues thereby acting as an adhesion barrier and preventing the formation of unwanted scar tissue.

Additional exemplary materials for surgical buttresses 500 for use with the surgical stapling devices disclosed herein are set forth in commonly assigned U.S. Pat. Nos. 5,542,594; 5,908,427; 5,964,774; and 6,045,560, and commonly assigned U.S. Application Publication Nos. 2006/0085034, filed on Apr. 20, 2006; and 2006/0135992, filed on Jun. 22, 2006, the entire contents of each of which is hereby incorporated herein by reference.

In an embodiment, surgical buttresses 500 may be fabricated from a suitable biocompatible and bioabsorbable material. Surgical buttresses 500 may also be fabricated from a non-absorbent material which does not retain fluid, for example, surgical buttresses 500 may be fabricated from "BIOSYN™" (a synthetic polyester, commercially available from Tyco Healthcare Group, LP d/b/a COVIDIEN, North Haven, Conn.), which is made from "GLYCOMER 631" (a block copolymer) which is a synthetic polyester composed of glycolide, dioxanone and trimethylene carbonate.

One block of the resulting copolymer contains randomly combined units derived from p-dioxanone (1,4-dioxan-2-one) and trimethylene carbonate (1,3-dioxan-2-one). A second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

Anvil buttress and/or cartridge buttress 500 may be pre-loaded (i.e., from the manufacturer) onto anvil assembly 300 or cartridge assembly 200. Additional or replacement buttresses 500 for anvil assembly 300 and/or cartridge assembly 200 may be secured to either anvil assembly 300 or cartridge assembly 200 as needed or desired.

In operation, with DLU 100 coupled to a distal end of elongated body 14 of surgical stapling apparatus 10, and with anvil and cartridge buttresses 500 pre-loaded onto anvil assembly 300 and cartridge assembly 200, respectively, surgical stapling apparatus 10 is used in accordance with methods known by those skilled in the art. Once anvil assembly 300 and cartridge assembly 200 are clamped onto tissue, surgical stapling apparatus 10 is fired. In firing surgical stapling apparatus 10, drive bar 150 is advanced from a proximal-most position to a distal-most position of DLU 100. In so doing, knife blade 156 of drive bar 150 enters notch 528 of buttress 500 thereby facilitating the dividing of buttress 500 and reducing any incidents of pushing or bunching-up of buttress 500 by blade 156. As drive bar 150 begins to travel distally, knife blade 156 substantially simultaneously cuts through a central section of the proximal anchors "S2, S4" of anvil assembly 300 and cartridge assembly 200, thereby respectively freeing the proximal ends of anvil and cartridge buttresses 500 therefrom. As knife blade 156 is moved distally, knife blade 156 slices or cuts longitudinally through both anvil buttress 500 and cartridge buttress 500, thereby dividing the buttresses 500 substantially in half.

Additionally, as drive bar 150 approaches the distal-most position, drive bar 150 and/or knife blade 156 engage a suture cutting assembly or suture release assembly, as described in U.S. patent application Ser. No. 12/342,400, filed on Dec. 23, 2008, the entire content of which is hereby incorporated herein by reference, to thereby sever or release distal sutures "S1 or S3" and thus release a distal end of buttress 500.

Figure 3:
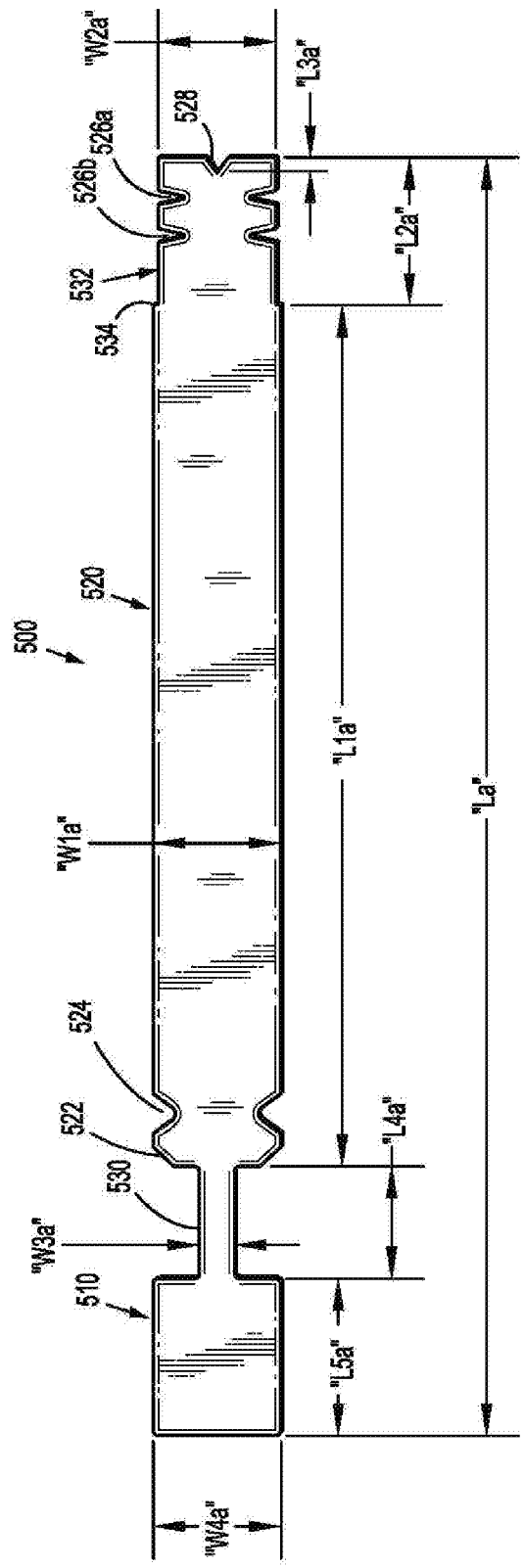
FIG. 3 is a top plan view of a buttress according to an embodiment of the present disclosure.
Figure 4:
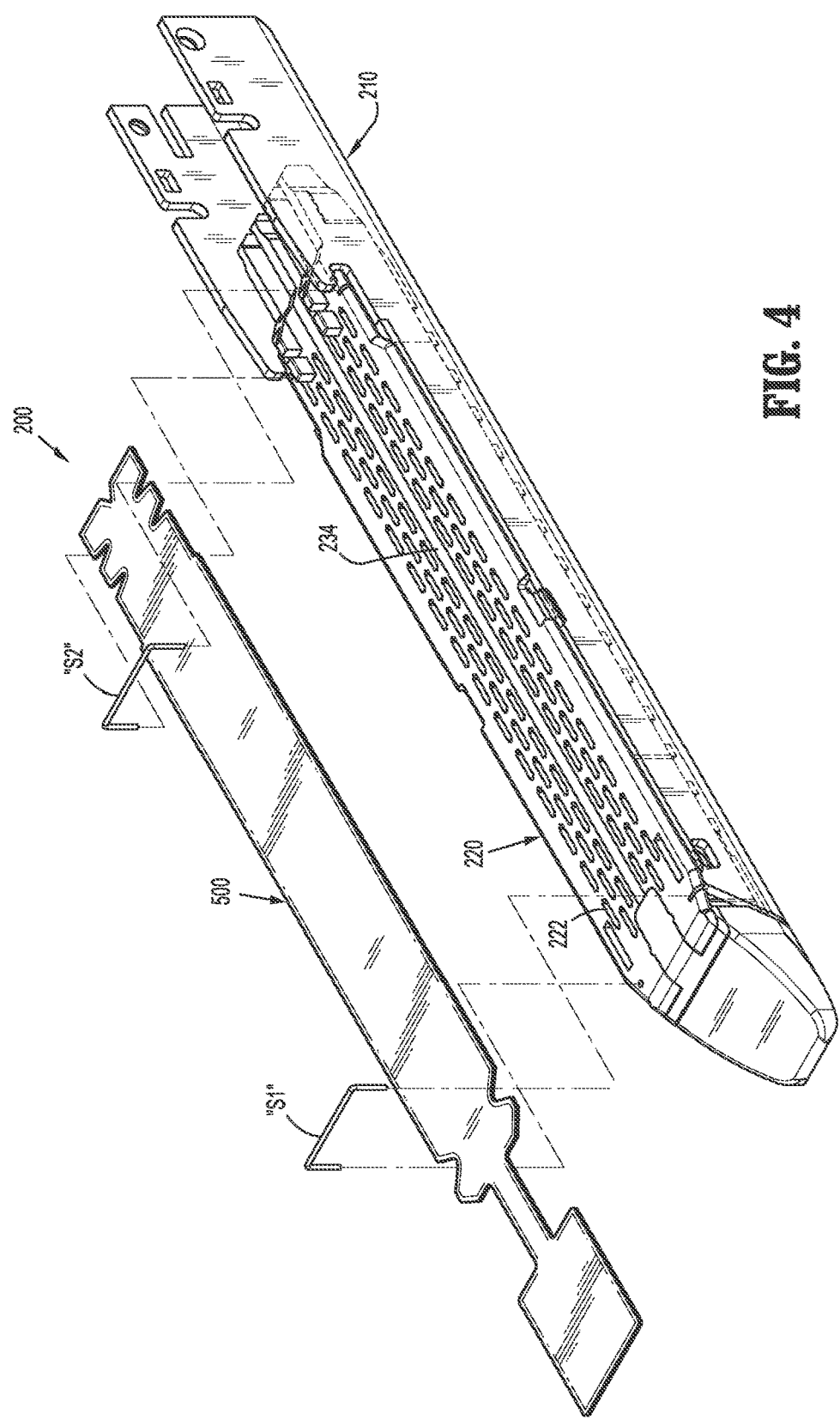
FIG. 4 is a top, perspective view of a cartridge half-section of the DLU of FIG. 2.
Figure 5:
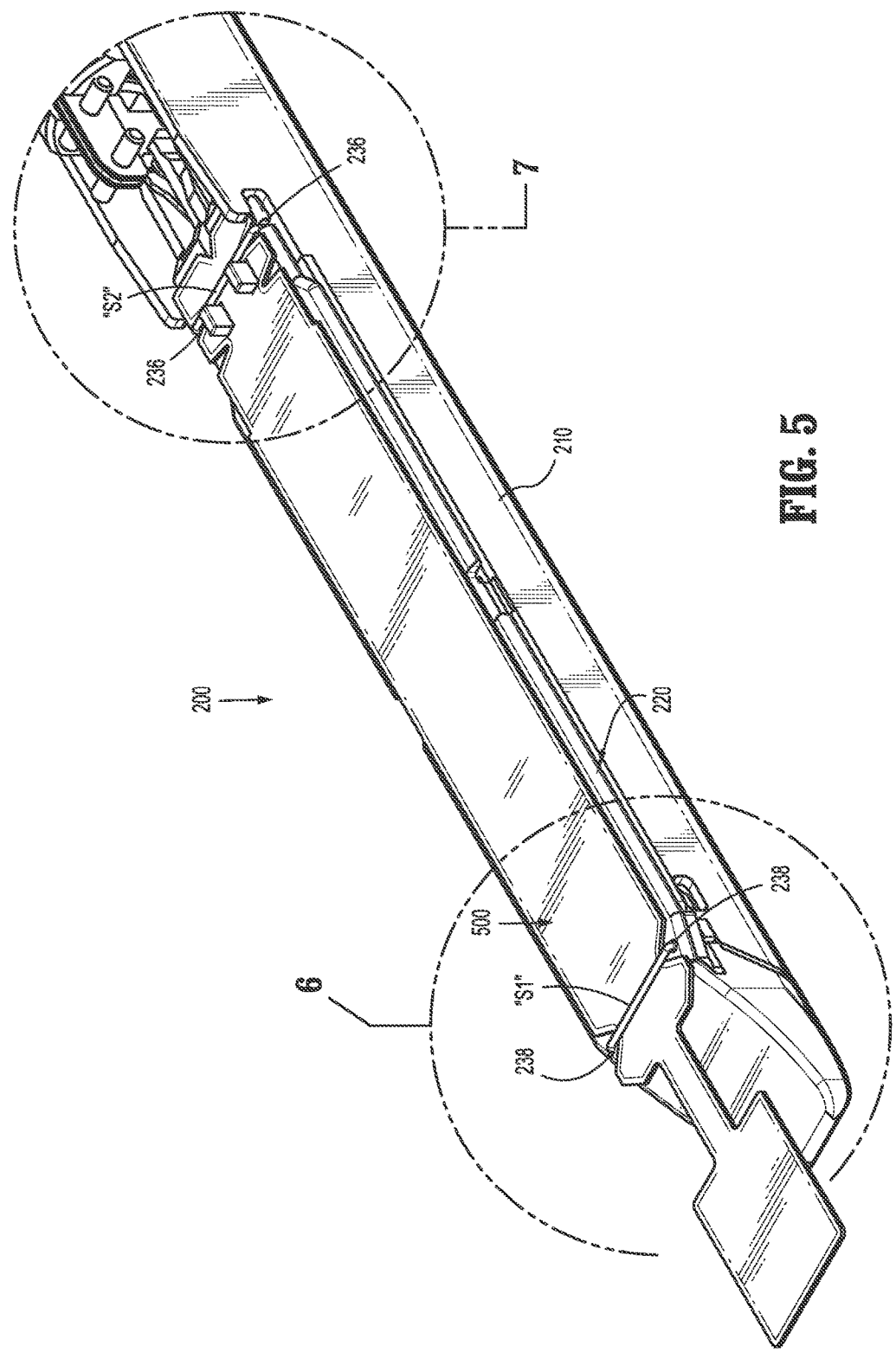
FIG. 5 is a perspective view of a cartridge assembly of the DLU of FIG. 2.
Figure 6:
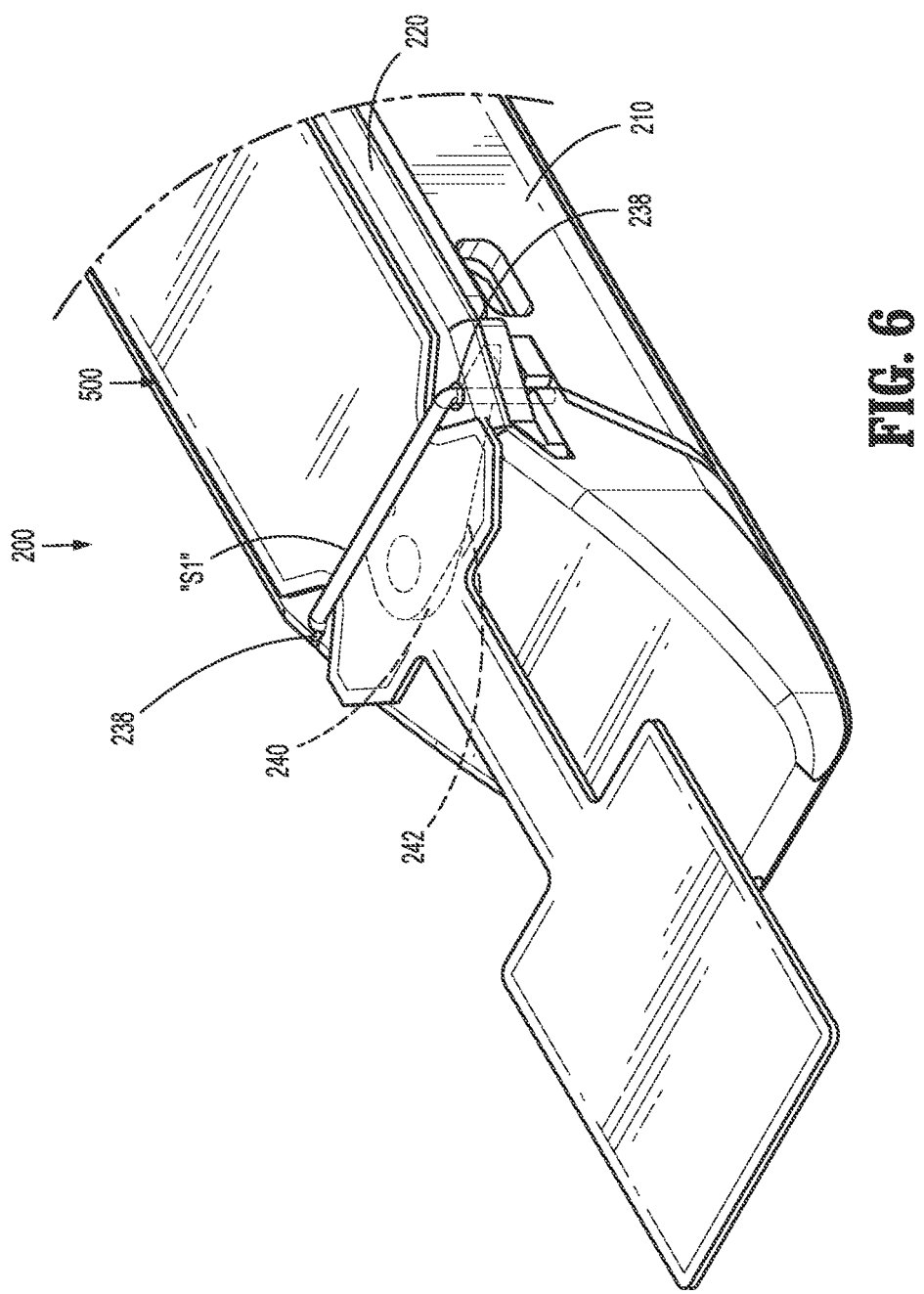
FIG. 6 is an enlarged perspective view of a distal end of the cartridge assembly of FIG. 5.
Figure 7:
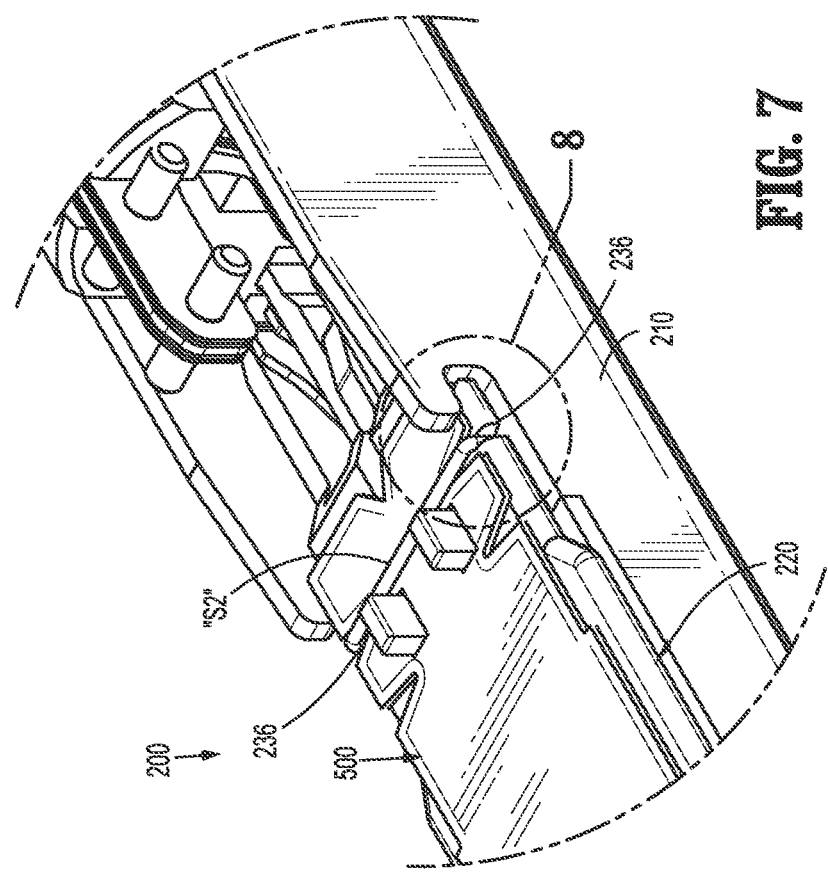
FIG. 7 is an enlarged view of the indicated area of detail of FIG. 5.
Figure 8:
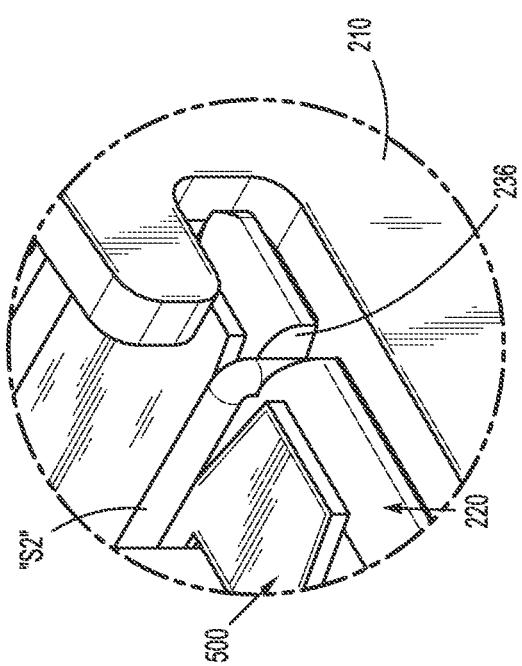
FIG. 8 is an enlarged view of the indicated area of detail of FIG. 7.

With reference to FIG. 3, an embodiment of a surgical buttress 500 having a uniform profile in accordance with the present disclosure is illustrated. Buttress 500 includes a head portion 510, a body portion 520, a neck portion 530 interconnecting head portion 510 and body portion 520, and a tail portion 532 extending proximally from body portion 520.

Buttress 500 is configured to be detachably secured to any sized anvil assembly 300 and/or cartridge assembly 200, as described above. Body portion 520 of buttress 500 defines a pair of opposing distal recesses 524 on transverse edges near a distal location 522 thereof. The pair of opposing distal recesses 524 may be utilized to secure body portion 520 to a distal end of anvil assembly 300 and/or cartridge assembly 200, either through a use of suture "S1 or S3" or any other type of fastener, e.g., staple. Distal portion 522 of body portion 520 has a reduced transverse cross-sectional dimension, e.g., angled, arcuate, so as to be suitable for various types of anvil and cartridge assemblies having different shapes.

Tail portion 532 of buttress 500 defines two pairs of opposing proximal recesses 526a, 526b formed therein. Each of the pair of proximal recesses 526a, 526b is disposed on a transverse side of tail portion 532 near the proximal edge thereof. Such proximal pair of recesses 526a, 526b serve to detachably secure tail portion 532 of buttress 500 to a proximal end of anvil assembly 300 and/or cartridge assembly 200. In order to accommodate various types of profiles, tail portion 532 of buttress 500 preferably has been provided with two pairs of opposing recesses, a first proximal pair of recesses 526a, and a second proximal pair of recesses 526b (located distal of the first proximal pair of recesses 526a). Each of the proximal pair of recesses 526a, 526b has a substantially v-shape profile.

In particular, when buttress 500 is to be used with a relatively longer anvil assembly 300 and/or cartridge assembly 200, then a suture "S2 or S4" is extended across tail portion 532 of buttress 500, passed through the proximal-most pair of recesses 526a of buttress 500, and secured to respective recesses 316 of anvil assembly 300 and/or recesses 236 of cartridge assembly 200. Moreover, when buttress 500 is to be used with a relatively shorter anvil assembly 300 and/or cartridge assembly 200, then a suture "S2 or S4" is extended across tail portion 532 of buttress 500, passed through the distal pair 526b of the proximal pair of recesses of buttress 500, and secured to respective recess 316 of anvil assembly 300 and/or recesses 236 of cartridge assembly 200.

According to another aspect of the present disclosure, a single profile or configuration buttress 500 may be used in connection with cartridge assembly 200 and/or anvil assembly 300. For example, the buttresses 500 that are used in connection with cartridge assembly 200 and anvil assembly 300 each may have the same overall length, width, thickness, perimetrical profile and material of construction.

In particular, as seen in FIG. 10, when buttress 500 is used in connection with cartridge assembly 200, a suture "S1" may extend transversely across a distal end portion of cartridge assembly 200 and captures or is otherwise secured to distal pair of recesses or attachment points 238 of cartridge assembly 200, wherein suture "S1" is in registration with distal recesses 524 of secure a distal end of body portion 520 of buttress 500. Additionally, when buttress 500 is used in connection with cartridge assembly 200, a suture "S2" may extend transversely across a proximal end portion of cartridge assembly 200 and captures or is otherwise secured to each of a proximal pair of recesses or attachment points 236 of cartridge assembly 200, wherein suture "S2" is in registration with the proximal-most pair 526a of the proximal pair of recesses of tail portion 532 of buttress 500.

With continued reference to FIG. 10, when buttress 500 is used in connection with anvil assembly 300, a suture "S3" may extend transversely across a distal end portion of anvil assembly 300 and captures or is otherwise secured to distal pair of recesses or attachment points 318 of anvil assembly 300, wherein suture "S3" is in registration with distal recesses 524 of secure a distal end of body portion 520 of buttress 500. Additionally, when buttress 500 is used in connection with anvil assembly 300, a suture "S4" may extend transversely across a proximal end portion of anvil assembly 300 and captures or is otherwise secured to each of a proximal pair of recesses or attachment points 316 of anvil assembly 300, wherein suture "S4" is in registration with the distal pair 526b of the proximal pair of recesses of tail portion 532 of buttress 500.

Neck portion 530 connects head portion 510 to a distal end of body portion 520. Generally, head portion 510 is in a substantially rectangular shape which is used as a tab to facilitate placement of buttress 500 in position on anvil assembly 300 and/or cartridge assembly 200. Following placement of buttress 500 on anvil assembly 300 and/or cartridge assembly 200, head portion 510 and neck portion 530 may be torn or otherwise cut away from body portion 520.

Tail portion 532 of buttress 500 includes a notch 528 at a proximal edge thereof. Notch 528 is substantially centered with respect to the longitudinal axis. Notch 528 which has a triangular or V-shape configuration may be utilized to provide a lead-in for the knife during a cutting of buttress 500. Notch 528 has a length "L3a", as seen in FIG. 3.

As seen in FIG. 3, buttress 500 has an overall length "La". Body portion 520 of buttress 500 has a length "L1a", and tail portion 532 has a length "L2a". Body portion 520 has a width "W1a" and tail portion 532 has a width "W2a" which is less that width "W1a" of body portion 520, wherein a shoulder 534 is defined between a side edge of body portion 520 and a side edge of tail portion 532. It is contemplated that a shoulder 534 is provided or defined along each opposed side edge of buttress 500.

With continued reference to FIG. 3, neck portion 530 of buttress 500 has a length "L4a", and head portion 510 has a length "L5a". Neck portion 530 of buttress 500 has a width "W3a" which is less that width "W1a" of body portion 520 and less than width "W2a" of tail portion 532. Also, head portion 510 has a width "W4a" which is substantially equal to width "W1a" of body portion 520.

The uniform profile of buttress 500 which simultaneously satisfies the requirements of one or more different assemblies offers advantages of simplifying the assembly process, minimizing the total number of unique components, and reducing assembly costs associated therewith.

Moreover, buttress 500 may be used on or in connection with cartridge assembly 200 and/or anvil assembly 300. In this manner, a single profile buttress 500 is produced and used for cartridge assembly 200 and/or anvil assembly 300. As such, the manufacturing and storage costs for buttresses 500 may be reduced.

As mentioned above, DLU 100 includes an anvil surgical buttress 500 and a cartridge surgical buttress 500 pre-loaded onto anvil assembly 300 and cartridge assembly 200. An exemplary method of loading anvil assembly 300 and/or cartridge assembly 200 with a buttress 500 will now be described.

During the manufacturing and/or assembly process of DLU 100, loading of anvil assembly 300 and/or cartridge assembly 200 with buttress 500 includes the step of placing a buttress 500 atop a tissue contacting surface of anvil assembly 300 and/or cartridge assembly 200 such that notch 528 of buttress is disposed near a proximal end of anvil assembly 300 and/or cartridge assembly 200 and head portion 510 of buttress 500 extends from a distal end of anvil assembly 300 and/or cartridge assembly 200. With buttress 500 so positioned against anvil assembly 300 and/or cartridge assembly 200, proximal sutures "S2" and/or "S4" are pulled down. Tension is then applied to buttress 500, in a distal direction, by pulling on head portion 510. Distal sutures "S1" and/or "S3" are then pulled down. At this time, all the sutures "S1-S4" are cinched in the respective attachment points 316, 318, 236, 238 of anvil assembly 300 and/or cartridge assembly 200. Following cinching of sutures "S1-S4," head portion 510 of buttress 500 may be released. Next, DLU 100 may be removed from a nesting and head portion 510 and neck portion 530 of buttress 500 may be removed or severed from body portion 520.

While the above-described embodiments surgical staplers incorporating the use of movable knife blades to sever and release surgical buttresses from the tissue contacting surfaces of the anvil assembly and the cartridge assembly have been shown and described in relation to endoscopic surgical staplers, it is envisioned and within the scope of the present disclosure that any of the embodiments disclosed herein may be incorporated into any type of surgical stapler, including and not limited to open surgical staplers, such as, for example, linear surgical staplers, circular staplers, and transverse surgical staplers.

Moreover, while only distal and proximal sutures have been shown and described as securing buttress 500 to anvil assembly 300 and/or cartridge assembly 300, it is contemplated that, in any of the embodiments disclosed herein, any number of transverse sutures may be provided along a length of the anvil assembly and/or cartridge assembly to aid with the securement of buttress 500 along a length thereof.

Any of the surgical buttresses disclosed herein may be comprised of the GLYCOMER 631 a block copolymer, or other polymers discussed above, as a film, non-woven, mesh or other type of material, and may also be made as a film, non-woven, mesh or other type of material, from poly-L-lactide (PLL), or Polycaprolactam (Nylon-6), or polyglycolic acid (PGA) each of which are homopolymers, or from glycolide trimethylene carbonate (Gly-TMC), which is a copolymer, PLL and Gly-TMC both being bio-degradable polyesters polymerized through a ring opening reaction. The non-woven material can be made utilizing a melt blown or spun bond process, or other known process. Non-woven materials and polymers are disclosed in U.S. patent application Ser. No. 13/293,215, entitled Hydrophilic Medical Devices, filed Nov. 10, 2011 (U.S. Patent Publication No. 2013-0123816), the disclosure of which is hereby incorporated by reference in its entirety. In certain embodiments, non-woven, felted, or other relatively supple materials having filaments are preferred.

Figure 11:
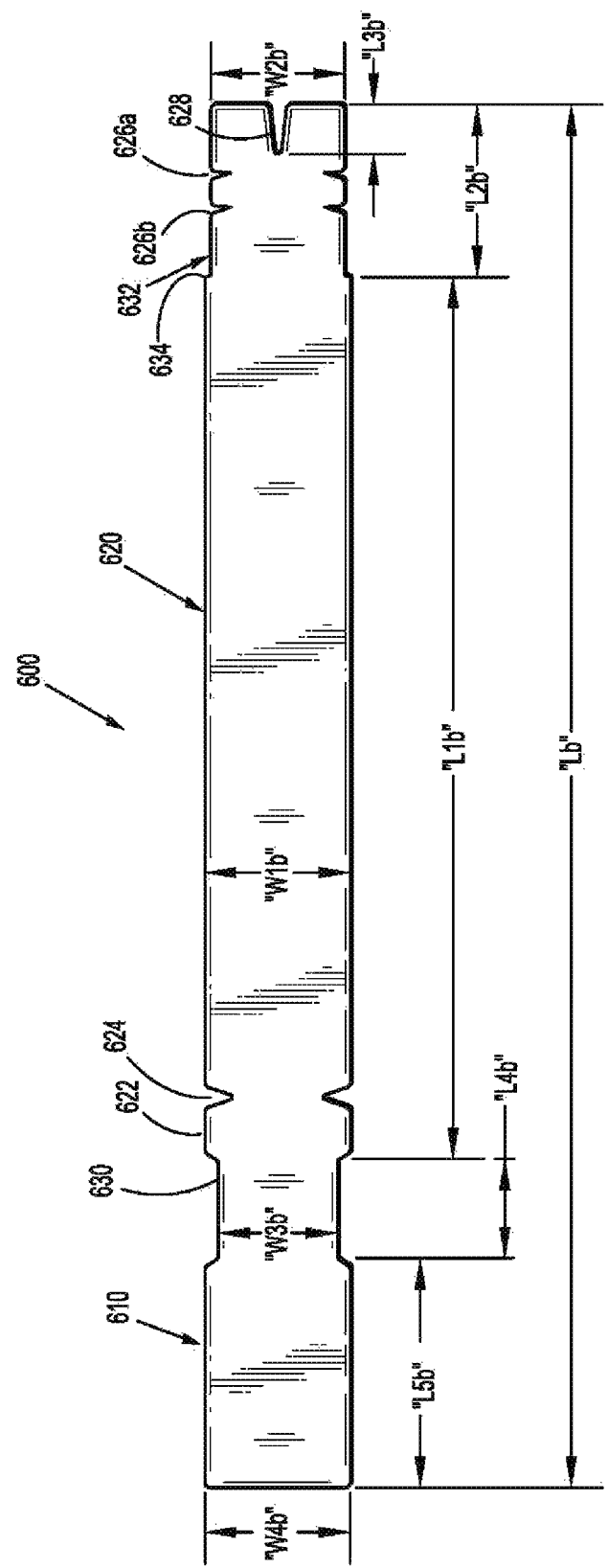
FIG. 11 is a top plan view of a buttress according to another embodiment of the present disclosure.

Turning now to FIG. 11, a surgical buttress having a uniform profile, in accordance with another embodiment of the present disclosure, is generally illustrated as 600. Buttress 600 includes a head portion 610, a body portion 620, a neck portion 630 interconnecting head portion 610 and body portion 620, and a tail portion 632 extending proximally from body portion 620.

Buttress 600, similar to buttress 500, is configured to be detachably secured to any sized anvil assembly 300 and/or cartridge assembly 200, as described above. Body portion 620 of buttress 600 defines a pair of opposing distal recesses 624 formed in opposed transverse side edges near a distal location 622 thereof.

In order to accommodate various types of profiles, tail portion 632 of buttress 600 includes two pairs of opposing recesses, a first proximal pair of recesses 626a, and a second proximal pair of recesses 626b (located distal of the first proximal pair of recesses 626a). Each of the proximal pair of recesses 626a, 626b has a substantially v-shape profile. Each of the proximal pair of recesses 626a, 626b is shallower as compared to the proximal pair of recesses 526a, 526b of tail portion 532 of buttress 500.

Neck portion 630 connects head portion 610 to a distal end of body portion 620. Generally, head portion 610 is in a substantially rectangular shape which is used as a tab to facilitate placement of buttress 600 in position on anvil assembly 300 and/or cartridge assembly 200. Following placement of buttress 600 on anvil assembly 300 and/or cartridge assembly 200, under at least certain circumstances, head portion 610 and neck portion 630 may be torn, damaged, or otherwise cut away from body portion 620.

Tail portion 632 of buttress 600 includes a notch 628 at a proximal edge thereof. Notch 628 is substantially centered with respect to the longitudinal axis. Notch 628 which has a U shaped configuration, a triangular, or V-shape configuration, and may be utilized to provide a lead-in for the knife during a cutting of buttress 600. Notch 628 has a length "L3b", as seen in FIG. 11. Length "L3b" of notch 628 of buttress 600 is greater than length "L3a" of notch 528 of buttress 500, and the notch 628 ends just before the first recesses 626a.

As seen in FIG. 11, buttress 600 has an overall length "Lb", which is greater than the overall length "La" of buttress 500. Body portion 620 of buttress 600 has a length "L1b", and tail portion 632 has a length "L2b". Body portion 620 has a width "W1b" and tail portion 632 has a width "W2b" which is less that width "W1b" of body portion 620, wherein a shoulder 634 is defined between a side edge of body portion 620 and a side edge of tail portion 632. It is contemplated that a shoulder 634 is provided or defined along each opposed side edge of buttress 600.

With reference to FIGS. 3 and 11, it is contemplated that body portion 620 of buttress 600 has a length "L1b" which is greater than length "L1a" of body portion 520 of buttress 500. Additionally, it is contemplated that tail portion 632 of buttress 600 has a length "L2b" which is greater than length "L2a" of tail portion 532 of buttress 500.

With reference back to FIG. 11, neck portion 630 of buttress 600 has a length "L4b", and head portion 610 has a length "L5b". Neck portion 630 of buttress 600 has a width "W3b" which is less that width "W1b" of body portion 620, and which is substantially equal to width "W2b" of tail portion 632. Also, head portion 610 has a width "W4b" which is substantially equal to width "W1b" of body portion 620.

With reference to FIGS. 3 and 11, it is contemplated that neck portion 630 of buttress 600 has a width "W3b" which is greater than width "W3a" of neck portion 530 of buttress 500. Additionally, it is contemplated that head portion 610 of buttress 600 has a length "L5b" which is greater than length "L5a" of head portion 510 of buttress 500.

Figure 12:
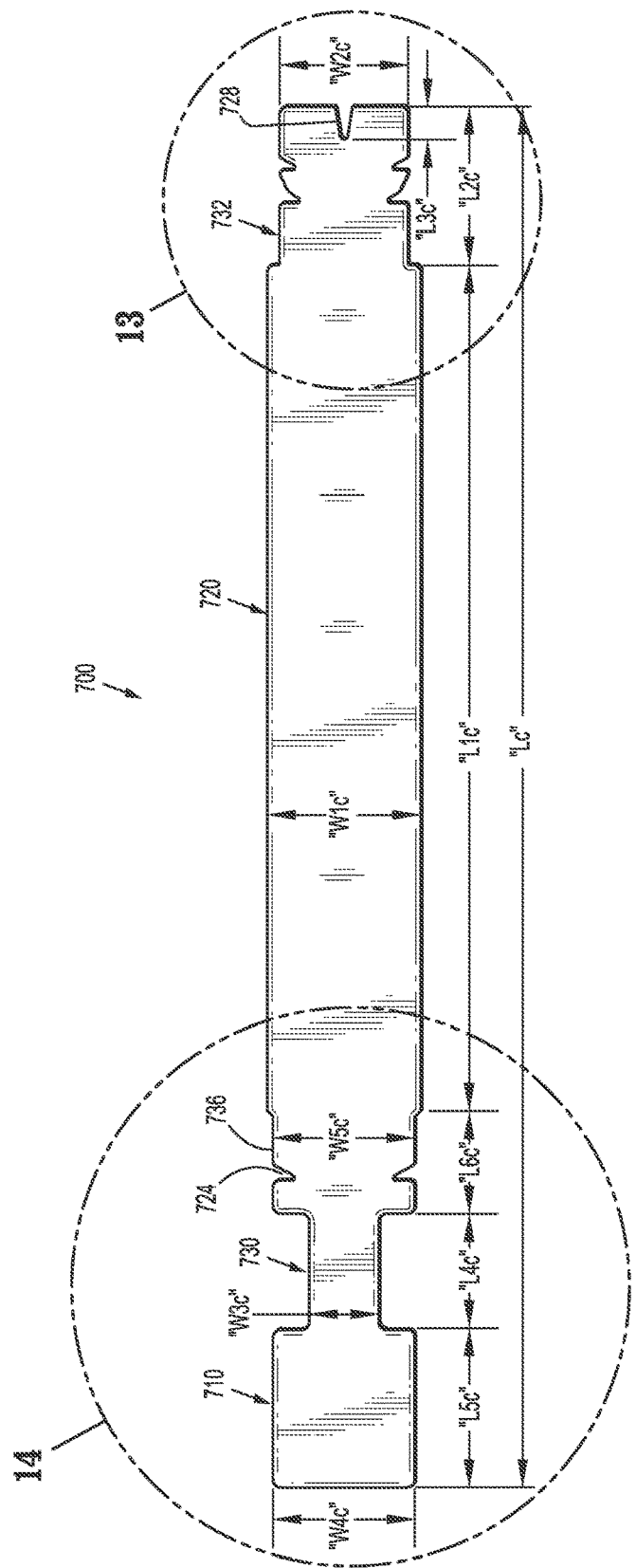
FIG. 12 is a top plan view of a buttress according to yet another embodiment of the present disclosure.
Figure 13:
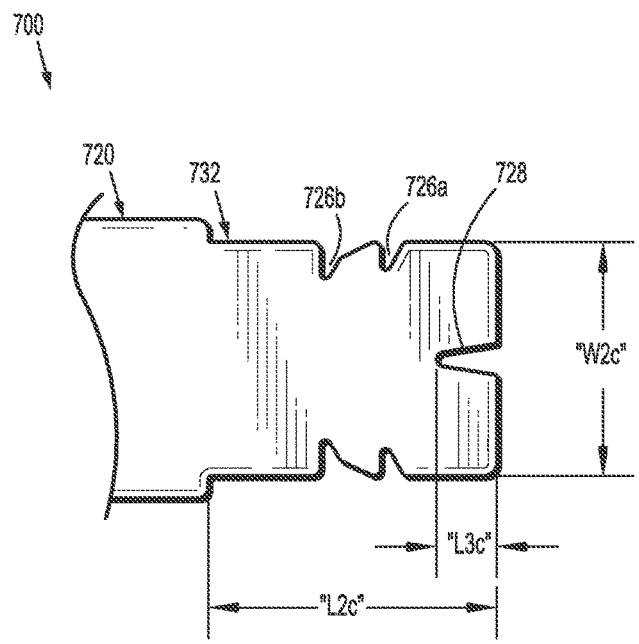
FIG. 13 is an enlarged view of the indicated area of detail of FIG. 12.
Figure 14:
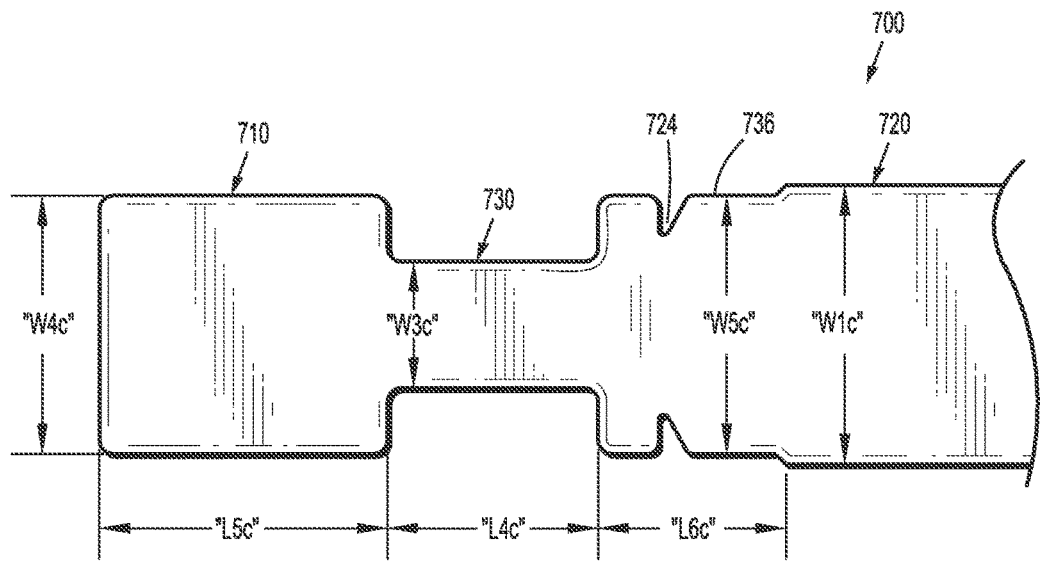
FIG. 14 is an enlarged view of the indicated area of detail of FIG. 12.

Turning now to FIGS. 12-14, a surgical buttress having a uniform profile, in accordance with yet another embodiment of the present disclosure, is generally illustrated as 700. Buttress 700 includes a head portion 710, a body portion 720, a nose portion 736 extending distally from body portion 720, a neck portion 730 interconnecting nose portion 736 and head portion 710, and a tail portion 732 extending proximally from body portion 720.

As illustrated in FIGS. 12-14, buttress 700 has an overall length "Lc", which is greater than the overall length "La" of buttress 500. Body portion 720 of buttress 700 has a length "L1c", tail portion 732 has a length "L2c", and nose portion 736 has a length "L6c". Body portion 720 has a width "W1c", tail portion 732 has a width "W2c" which is less than width "W1c" of body portion 720, wherein a shoulder is defined between a side edge of body portion 720 and a side edge of tail portion 732, and nose portion 736 has a width "W5c" which is less than width "W1c" of body portion 720, wherein a shoulder is defined between a side edge of body portion 720 and a side edge of nose portion 736. It is contemplated that shoulders are provided or defined along each opposed side edge of buttress 700.

With reference to FIGS. 3, 12 and 13, it is contemplated that body portion 720 of buttress 700 has a length "L1c" which is greater than length "L1a" of body portion 520 of buttress 500. Additionally, it is contemplated that tail portion 732 of buttress 700 has a length "L2c" which is greater than length "L2a" of tail portion 532 of buttress 500.

With reference back to FIGS. 12 and 14, nose portion 736 of buttress 700 has a length "L6c."

Neck portion 730 of buttress 700 has a length "L4c", and head portion 710 of buttress 700 has a length "L5c". Neck portion 730 of buttress 700 has a width "W3c" which is less that width "W5c" of nose portion 736. Head portion 710 of buttress 700 has a width "W4c" which is substantially equal to width "W5c" of nose portion 736.

With reference to FIGS. 12 and 13, it is contemplated that neck portion 730 of buttress 700 has a width "W3c" which is greater than width "W3a" of neck portion 530 of buttress 500. Additionally, it is contemplated that head portion 710 of buttress 700 has a length "L5c" which is substantially equal to length "L5a" of head portion 510 of buttress 500.

Buttress 700, similar to buttress 600, is configured to be detachably secured to any sized anvil assembly 300 and/or cartridge assembly 200, as described above. Buttress 700 defines a pair of opposing distal recesses 724 formed in opposed transverse side edges of nose portion 736. Each distal recess 724 has a substantially v-shaped profile. Specifically, each distal recess 724 includes a distal portion that is oriented orthogonal to a longitudinal axis of buttress 700, and a proximal portion that is oriented transverse to the longitudinal axis of buttress 700. In an embodiment, the proximal portion of each distal recess 724 may be oriented at about a 63° angle relative to the longitudinal axis of buttress 700.

In order to accommodate various types of profiles, tail portion 732 of buttress 700 includes two pairs of opposing recesses, a first proximal pair of recesses 726a, and a second proximal pair of recesses 726b (located distal of the first proximal pair of recesses 726a). Each of the proximal pair of recesses 726a, 726b has a substantially v-shaped profile.

Specifically, each recess of the first proximal pair of recesses 726a and each recess of the second proximal pair of recesses 726b includes a distal portion that is oriented orthogonal to a longitudinal axis of buttress 700, and a proximal portion that is oriented transverse to the longitudinal axis of buttress 700. In an embodiment, the proximal portion of each of the first and second proximal pair of recesses 726a, 726b may be oriented at about a 60° angle relative to the longitudinal axis of buttress 700.

As best illustrated in FIG. 13, the segment or portion of side edges of tail portion 732, located between the first proximal pair of recesses 726a and the second proximal pair of recesses 726b, is angled or tapers towards the longitudinal axis of buttress 700, from a proximal end to a distal end thereof.

With reference to FIGS. 12 and 13, neck portion 730 connects head portion 710 to a distal end of nose portion 736. Generally, head portion 710 is in a substantially rectangular shape which is used as a tab to facilitate placement of buttress 700 in position on anvil assembly 300 and/or cartridge assembly 200. Following placement of buttress 700 on anvil assembly 300 and/or cartridge assembly 200, under at least certain circumstances, head portion 710 and neck portion 730 may be torn, damaged, or otherwise cut away from nose portion 736.

Tail portion 732 of buttress 700 includes a notch 728 at a proximal edge thereof. Notch 728 is substantially centered with respect to the longitudinal axis of buttress 700. Notch 728 may have a U shaped configuration, a triangular, or V-shape configuration, and may be utilized to provide a lead-in for the knife during a cutting of buttress 700. Notch 728 has a length "L3c", as seen in FIGS. 12 and 13. Length "L3c" of notch 728 of buttress 700 is greater than length "L3a" of notch 528 of buttress 500, and the notch 728 ends just before the first recesses 726a.

Figure 15:
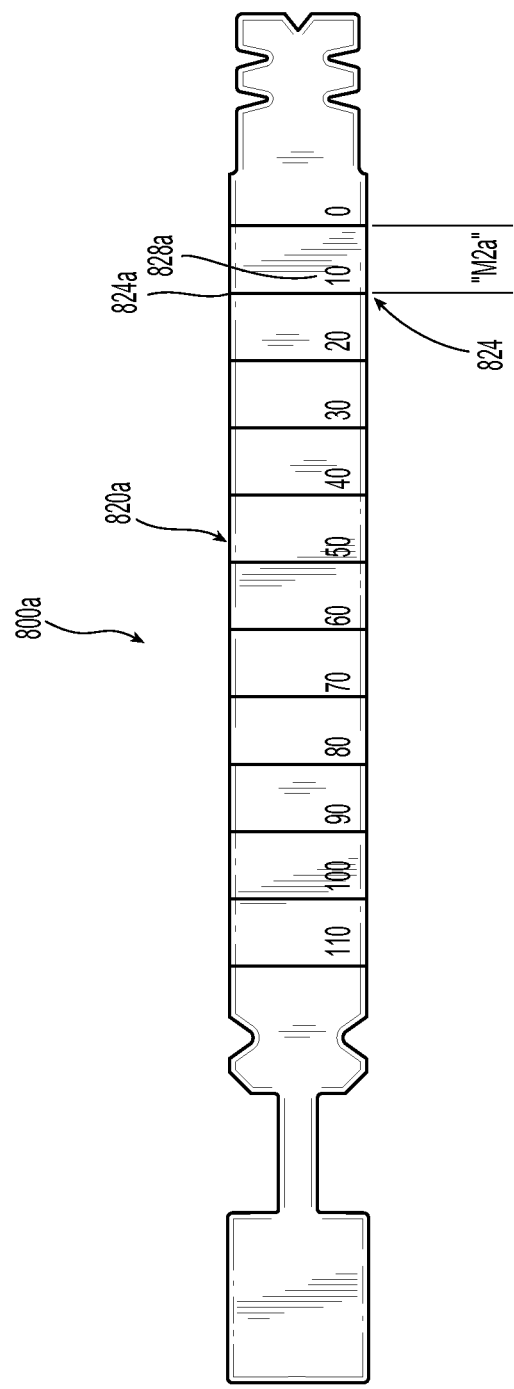
FIG. 15 is a top plan view of a buttress according to another embodiment of the present disclosure.

With reference to FIG. 15, a surgical buttress 800a having a uniform profile in accordance with another embodiment of the present disclosure is illustrated. Buttress 800a, similar to buttress 600, is configured to be detachably secured to any sized anvil assembly 300 and/or cartridge assembly 200, as described above.

Surgical buttress 800a includes a body portion 820a having at least one marking 824 disposed therein and/or thereon. Marking(s) 824 include indicia, e.g. patterns, shapes, alphanumeric labeling, etc., to indicate a length of the staple line. As illustrated in FIG. 15, marking(s) 824 may be formed of biocompatible or bioabsorbable ink, and/or radiopaque ink or material, that is imprinted longitudinally along the body portion 820a as lines 824a and/or numerals 828a. Line marking(s) 824a may be oriented orthogonal to the longitudinal axis of the buttress 800a and may extend across an entire width of the body portion 820a. Additionally, it is contemplated that a plurality of line markings 824a may be equidistant to one another defining a distance "M2a" between adjacent line markings 824a. It is contemplated that the markings can be formed using radiopaque inks and/or materials.

Figure 16:
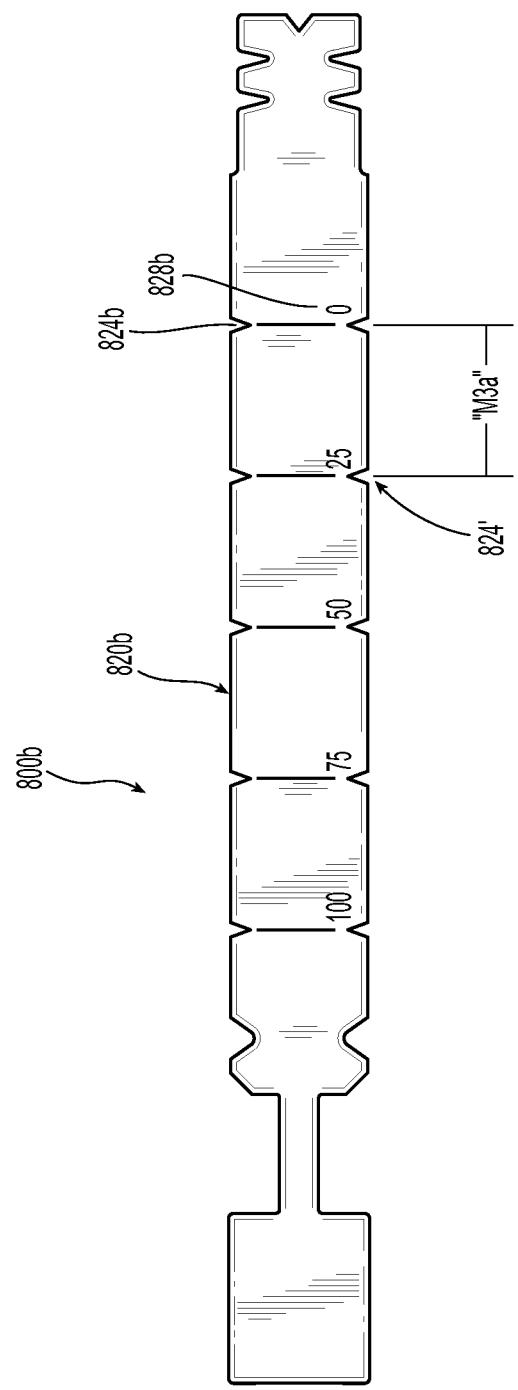
FIG. 16 is a top plan view of a buttress according to another embodiment of the present disclosure.

Referring now to FIG. 16, a surgical buttress 800b having a uniform profile in accordance with another embodiment of the present disclosure is illustrated. Buttress 800b, similar to buttress 800a, is configured to be detachably secured to any sized anvil assembly 300 and/or cartridge assembly 200, as described above.

Surgical buttress 800b includes a body portion 820b having at least one marking 824' disposed therein. Marking(s) 824' include indicia and/or recesses, score lines, embossing, etc., to indicate a length of the staple line. As illustrated in FIG. 16, marking(s) 824' may be formed of biocompatible or bioabsorbable ink, and/or radiopaque ink, as numerals 828b and as a series of recesses or notches 824b extending longitudinally along the body portion 820b. Recesses 824b may be V-shaped and disposed, one each, on opposing sides of the body portion 820b. Additionally, it is contemplated that a plurality of recesses 824b may be equidistant to one another defining a distance "M3a" between adjacent recesses 824b.

It is contemplated that, in any of the embodiments disclosed herein, markings such as those disclosed herein can be pre-incorporated in a surgical buttress to identify tissue or specimen structures after surgical resection with a surgical instrument or surgical stapler. The markings can be applied during the manufacturing process by methods including thermal or laser processes, printing, sewing, stamping, cutting, dyeing, etc. Alternatively, the markings can be placed by forming notches or holes. Any inks or sewn structures must be biocompatible materials and would desirably be bioabsorbable. It is contemplated that the markings can be used to identify the margins of diseased tissue. For example, the buttress material will be present on the tissue remnant and the specimen removed. A pathologist can communicate to a surgeon the location of any tissue having anomalies with reference to the markings.

Figure 17:
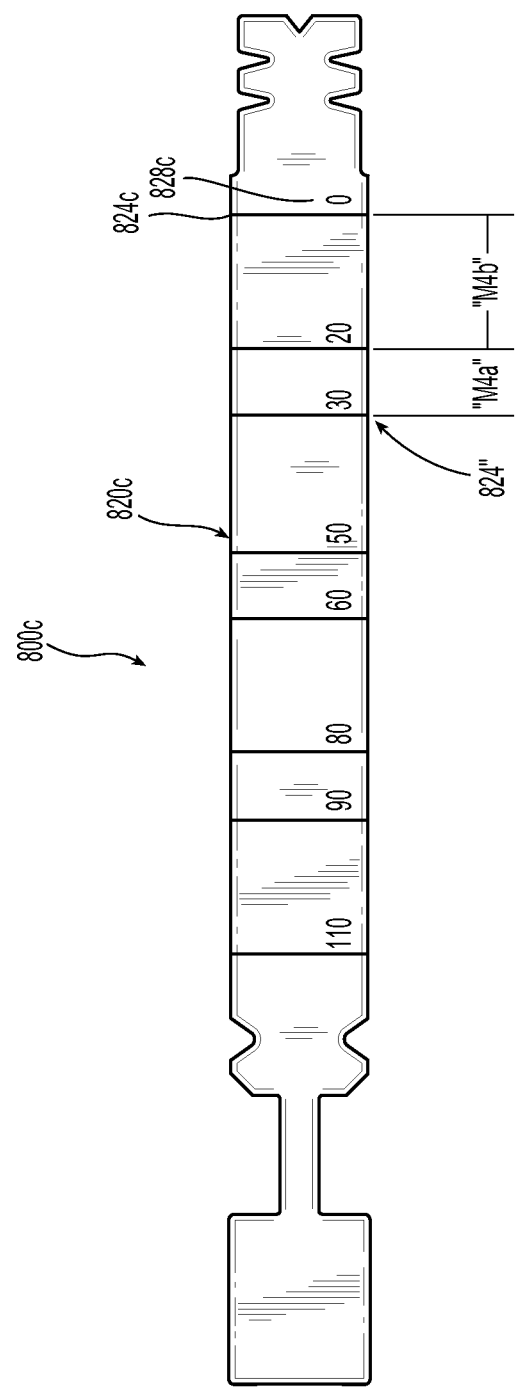
FIG. 17 is a top plan view of a buttress according to another embodiment of the present disclosure.

With reference to FIG. 17, a surgical buttress 800c having a uniform profile in accordance with another embodiment of the present disclosure is illustrated. Buttress 800c, similar to buttress 800a, is configured to be detachably secured to any sized anvil assembly 300 and/or cartridge assembly 200, as described above. The buttress 800c can be provided separately and attached to a surgical instrument by the user, or it can be pre-loaded on an instrument, as discussed above.

Surgical buttress 800c includes a body portion 820c having at least one marking 824" disposed therein and/or thereon. Marking(s) 824" include indicia, e.g. patterns, shapes, alphanumeric labeling, etc., to indicate a length of the staple line. As illustrated in FIG. 17, marking(s) 824" may be formed of biocompatible or bioabsorbable ink that is imprinted longitudinally along the body portion 820c as lines 824c and/or numerals 828c. Line marking(s) 824c may be oriented orthogonal to the longitudinal axis of buttress 800c and may extend across an entire width of the body portion 820c. Additionally, it is contemplated that a plurality of line markings 824c may not be equidistant to one another defining, for example, a distance "M4a" between a first line marking $824c_1$ and a second line marking $824c_2$ and a distance "M4b" between a second line marking $824c_2$ and an adjacent line marking or third line marking $824c_3$.

Figure 18:
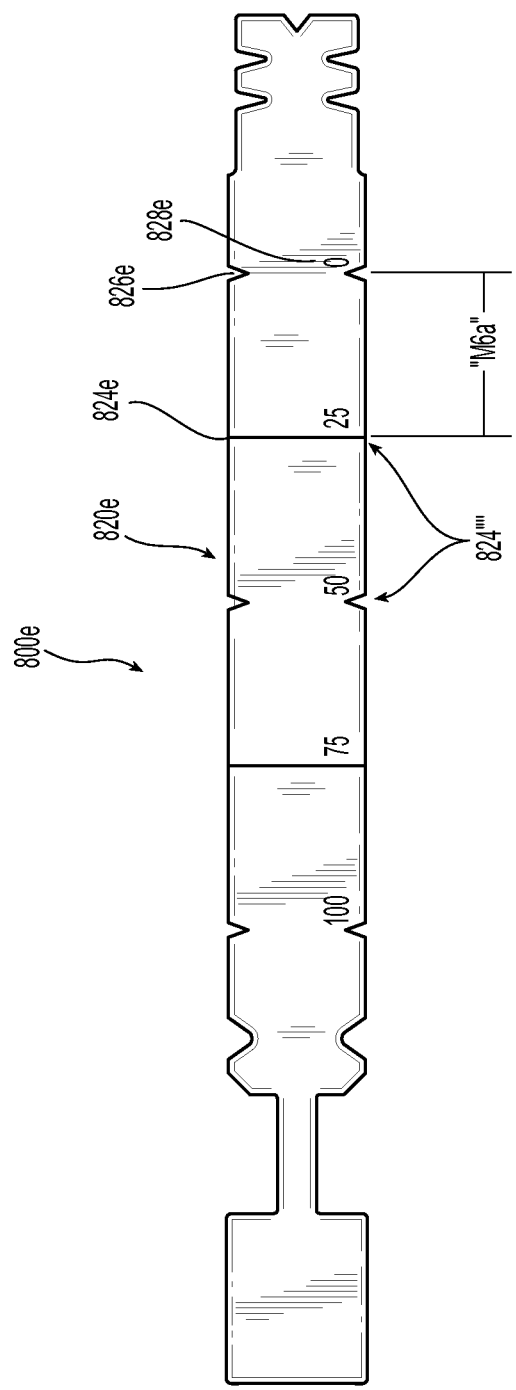
FIG. 18 is a top plan view of a buttress according to another embodiment of the present disclosure.

Referring now to FIG. 18, a surgical buttress 800e having a uniform profile in accordance with another embodiment of the present disclosure is illustrated. Buttress 800e, similar to buttress 800a, is configured to be detachably secured to any sized anvil assembly 300 and/or cartridge assembly 200, as described above.

Surgical buttress 800e includes a body portion 820e having at least one marking 824"" disposed therein. Marking(s) 824"" include indicia and/or recesses, score lines, embossing, etc., to indicate a length of the staple line. As illustrated in FIG. 18, marking(s) 824"" may be formed of biocompatible or bioabsorable ink that is imprinted longitudinally along the body portion 820e as lines 824e and/or numerals 828e. The markings(s) 824"" may further include a series of recesses 826e extending longitudinally along the body portion 820e. Recesses 826e may be V-shaped and disposed, one each, on opposing sides of the body portion 820e. Additionally, it is contemplated that a plurality of recesses 826e and line markings 824e are positioned in an alternating pattern and may be equidistant to one another defining a distance "M6a" between the line marking 824e and adjacent recess 826e.

Figure 19:
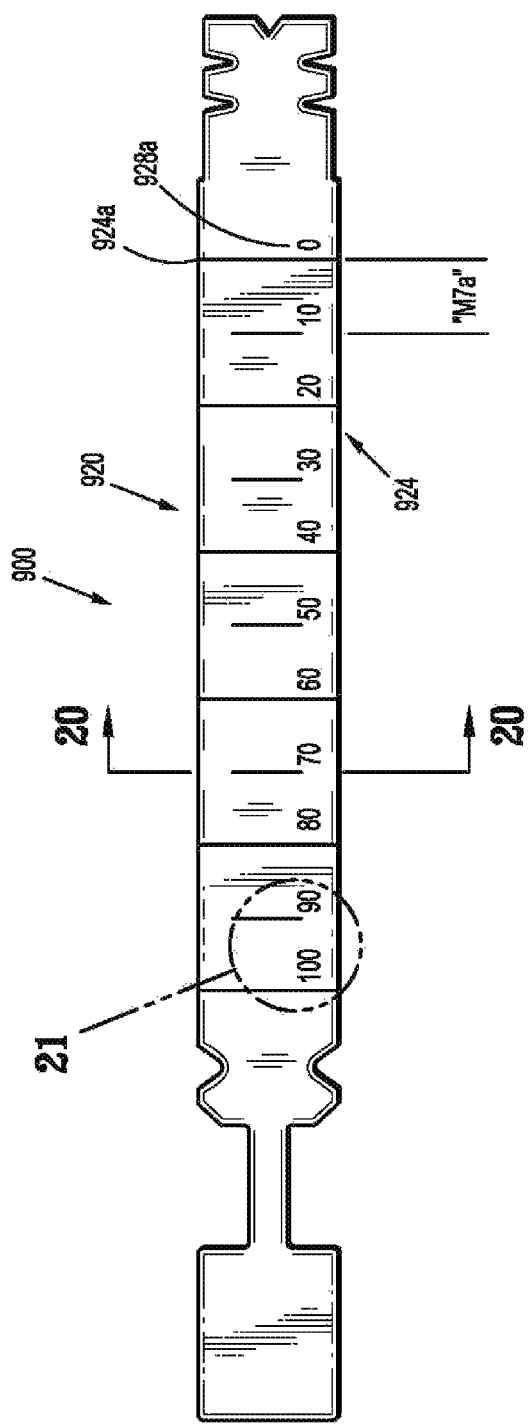
FIG. 19 is a top plan view of a buttress according to another embodiment of the present disclosure.

Now turning to FIG. 19, a surgical buttress 900 having a uniform profile in accordance with another embodiment of the present disclosure is illustrated. Buttress 900, similar to buttress 800a, is configured to be detachably secured to any sized anvil assembly 300 and/or cartridge assembly 200, as described above.

Surgical buttress 900 includes a body portion 920 having at least one marking 924 disposed therein and/or thereon. Marking(s) 924 include indicia, e.g. patterns, shapes, alphanumeric labeling, etc., to indicate a length of the staple line. As illustrated in FIG. 19, marking(s) 924 may be formed of biocompatible or bioabsorable ink that is imprinted longitudinally along the body portion 920 as lines 924a and/or numerals 928a. Line marking(s) 928a may be oriented orthogonal to the longitudinal axis of buttress 900 and may vary in length thereby extending across a percentage or an entire width of the body portion 920. Additionally, it is contemplated that a plurality of line markings 924a may be equidistant to one another defining a distance "M7a" between adjacent line markings 924a. It is contemplated that any of the embodiments disclosed herein can include the markings disclosed.

In any of the embodiments disclosed herein, the surgical buttress can further include at least one source of radioactive material disposed in or on the body portion of the buttress.

The radioactive material 940 is disposed in and/or on the body portion 920 and includes encapsulated radioactive isotopes. It is envisioned that the radioactive material 940 is formed as brachytherapy seeds and the seeds may be embedded into the body portion 920 of the surgical buttress 900 prior to loading the surgical buttress 900 into the anvil assembly 300 and/or cartridge assembly 200. Radioactive material 940 may take the form of individual radioactive seeds/capsules or radioactive seeds/capsules incorporated into a biocompatible or bioabsorbable thread or the like.

Figure 20:
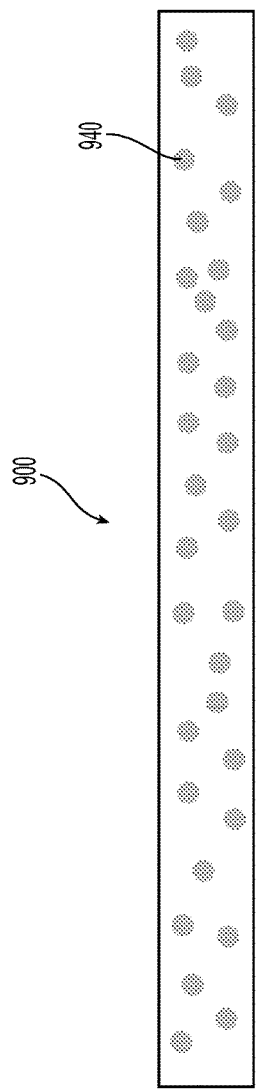
FIG. 20 is a cross-sectional view, as taken through 20-20 of FIG. 19.

As illustrated in FIG. 20, the radioactive material 940 may be scattered throughout the body portion 920 at varying depths. Alternatively, the radioactive material 940 may be disposed evenly throughout the body portion 920. Additionally, the radioactive material 940 may be deposited on or into a section of the body portion 920. Further, radioactive material 940 may be disposed solely along each lateral side edge of body portion 920 of surgical buttress 900. In this manner, radioactive material 940 is not affected, impacted or disturbed by any staples being fired by the stapling apparatus or by the knife blade that is advanced during a firing of the stapling apparatus. It is contemplated that any of the embodiments disclosed herein can include the radioactive material.

It is contemplated that the process of embedding the radioactive material 940 into the surgical buttress 900 includes inserting the radioactive material 940 into a template (not shown) capable of holding the radioactive material 940, then mating or abutting the template with the surgical buttress 900 and embedding the radioactive material 940 into the body portion 920 of the surgical buttress 900.

Figure 21:
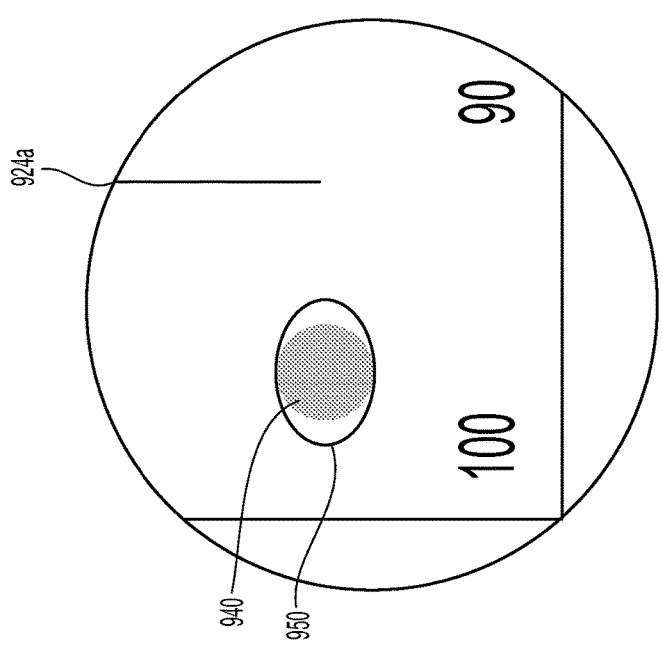
FIG. 21 is an enlarged view of the indicated area of detail of FIG. 19.

As illustrated in FIG. 21, the radioactive material 940 may be in the form of a seed embedded into a pore 950 or pocket disposed in the surgical buttress 900. For example, the pore 950 may be formed while mating the template with the surgical buttress 900 prior to embedding the radioactive material 940 therein.

Figure 22:
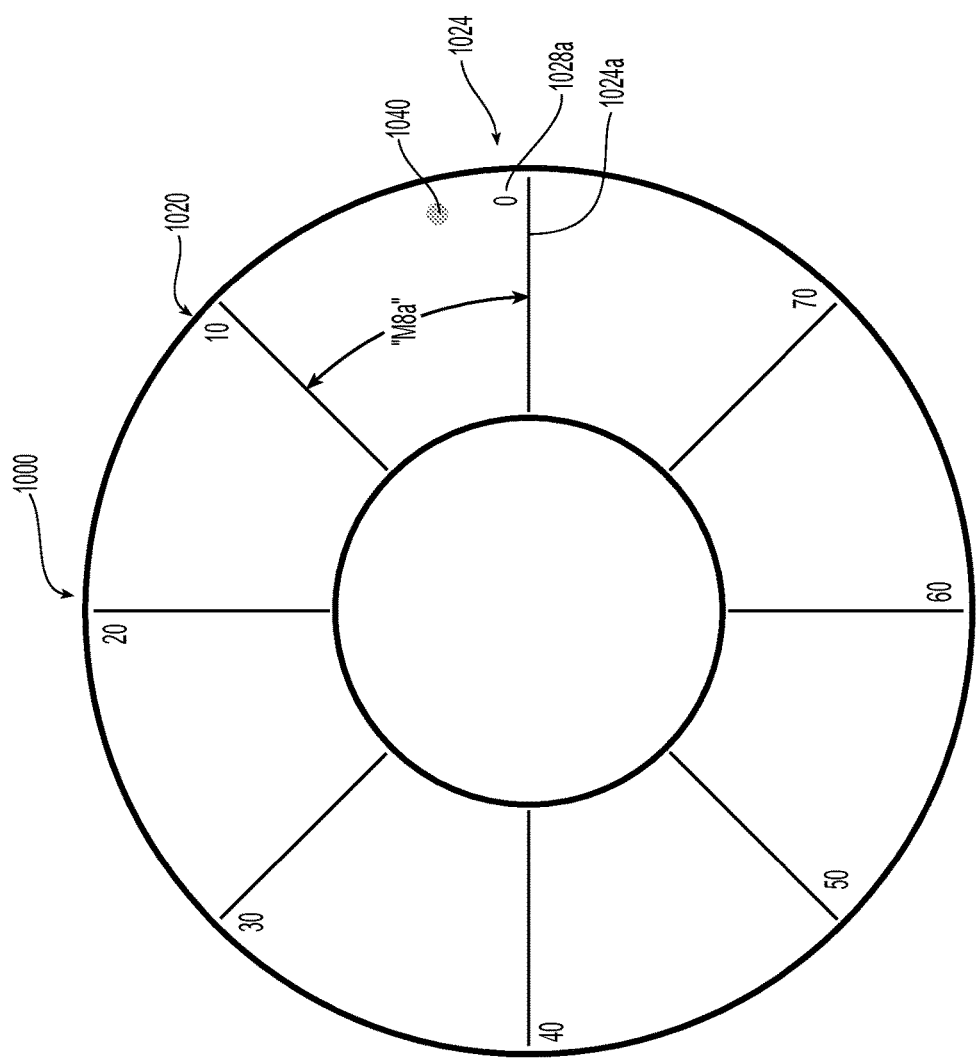
FIG. 22 is a top plan view of a buttress according to another embodiment of the present disclosure.

Now turning to FIG. 22, a surgical buttress 1000 having a uniform profile in accordance with another embodiment of the present disclosure is illustrated. Surgical buttress 1000 includes a body portion 1020 that is annular in shape having at least one marking 1024 disposed therein and/or thereon. Marking(s) 1024 include indicia, e.g. patterns, shapes, alphanumeric labeling, etc., to indicate an arc length of the staple line. As illustrated in FIG. 22, marking(s) 1024 may be formed of biocompatible or bioabsorable ink, and/or radiopaque material, that is imprinted radially about the body portion 1020 as lines 1024a and/or numerals 1028a. Line marking(s) 1024a may be oriented radial to a central axis of body portion 1020 and may extend across an entire radius of the body portion 1020. Additionally, it is contemplated that a plurality of line markings 1024a may be radially disposed, equidistant to one another, defining an arc length "M8a" between adjacent line markings 1024a.

With reference still to FIG. 22, surgical buttress 1000 further includes at least one radioactive material 1040 disposed in and/or on the body portion 1020. It is envisioned that the radioactive material 1040 is formed as brachytherapy seed(s) and the seed(s) may be embedded into the body portion 1020 of the surgical buttress 1000 prior to loading the surgical buttress 1000 into a surgical stapling device.

Additionally, the radioactive material 1040 may be deposited on or into a section of the body portion 1020. It is contemplated that the process of embedding the radioactive material 1040 into the surgical buttress 1000 includes inserting the radioactive material 1040 into a template (not shown) capable of holding the radioactive material 1040, then mating the template with the surgical buttress 1000 and embedding the radioactive material 1040 into the body portion 1020 of the surgical buttress 1000. The radioactive material 1040 may be embedded into a pore or pocket (not shown) disposed in the surgical buttress 1000. For example, the pore or pocket (not shown) may be created while mating the template with the surgical buttress 1000 prior to embedding the radioactive material 1040.

In any of the embodiments disclosed herein, the buttresses may be incorporated into, or configured for use with, devices that are part of a powered surgical system or robotic surgical system.

It is also contemplated that, for any of the buttresses disclosed herein, the buttress can have pre-formed (e.g., by the manufacturer) pockets or pores configured and arranged for the receipt of the radioactive material discussed above. It is contemplated that brachytherapy seeds can be separately packaged and provided, with or without a template, and that the user can apply the seeds to the buttress or buttresses. For example, the user (such as a surgeon or operating room nurse) can place a seed into one or more of the pockets or pores discussed above. It is contemplated that the pockets or pores are pre-formed in the buttress, whether pre-loaded on a surgical instrument or not. In certain embodiments, the pockets or pores are disposed on the lateral edges of the surgical buttress as shown in FIGS. 23-25. The buttress may be configured with lateral wings that extend beyond the sides of the surgical stapler jaws. In any of the embodiments disclosed herein, the buttress material may be porous and configured to encourage tissue ingrowth.

FIG. 23 shows a surgical buttress 1010 having a series of markings, which may be formed as discussed above. The markings 1020a can have a pattern 1020 that would aid a surgeon, operating room nurse, and/or pathologist in identifying the location of certain tissue that was excised from the body. For example, the pattern shown has alternating shorter and longer lines, however, other patterns may be used. The buttress 1010 has a central, proximally located notch 1022 at the location where a knife of a surgical stapler will cut through tissue, to aid the advancement of the knife. Such notch 1022 may be triangular or oblong in shape.

The surgical buttress 1010 can have wings or lateral edges 1024, along the long sides of the buttress, which extend beyond the sides of the staple cartridge 1030. Such wings 1024 can include or incorporate pockets or pores for the receipt of radioactive material. For example, brachytherapy seeds, which may be configured as discussed herein, can be inserted in the pockets or pores 1025. This can be done by the manufacturer, or by the surgeon or operating room nurse whether or not the staple cartridge assembly has a pre-loaded buttress. A tool 1040, which can be a tweezer or a specially designed device, can be used to safely insert the seed or seeds 1026 into the pockets or pores 1025. One advantage of having a plurality of pockets or pores along the length of the side edges of the buttress 1010 is that the surgeon or operating room nurse can insert seeds 1026 in some or all of the pockets, on one or more sides of the buttress, or may do so in some advantageous pattern.

Although a linear surgical stapling cartridge and buttress is shown, other types are contemplated. For example, a buttress for a circular stapler could have an outer circular edge with a wing or flange that incorporates or includes pockets or pores.

It is contemplated that the radioactive material can come in other forms. For example, the wings, or flanges, can be provided, and a suture or strand having radioactive material inside or on it, can be threaded through the wing or flange. It is contemplated that the radioactive material can be provided as brachytherapy seeds that are installed in pockets that are adhesively attached to the wing or flange of the surgical buttress. It is contemplated that the radioactive material is attached to a surgical buttress at locations other than the lateral sides or outer circular edge.

It is contemplated that a surgical buttress having markings as discussed herein may or may not include the radioactive material or means for attaching radioactive material. It is contemplated that a surgical buttress having the radioactive material or means for attaching radioactive material as discussed herein may or may not include markings.

The present disclosure also includes a surgical kit 1 having a surgical stapling instrument 2, at least one surgical buttress 3, and a separate package 4 of encapsulated radioactive material 5, as shown in FIG. 26. The surgical stapling instrument 2 can be a circular stapler. The surgical stapling instrument 2 can be a surgical stapling loading unit. The loading unit can be a staple cartridge assembly. The at least one surgical buttress 3 may be pre-loaded onto the surgical stapling instrument 2. The at least one surgical buttress 3 can include pockets. The at least one surgical buttress 3 can be formed with lateral sides or edges and can include pockets on the lateral sides or edges of the at least one buttress 3. The lateral sides or edges can include wings that are configured to extend beyond the edges of the cartridge and/or surgical stapling instrument jaws. The encapsulated radioactive material 5 may include radioactive isotopes, such as iodine or cesium isotopes, and may be brachytherapy seeds. The package 4 can include shielding (e.g., for the isotopes). The package 4 can include a template 6 and the isotopes 5 can be attached to the template 6.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A surgical buttress for use in a surgical stapling apparatus, the surgical buttress comprising a body portion and lateral sides extending from opposed edges of the body portion, each of the lateral sides defining pockets therein and each of the pockets having a width extending from the edge of the body portion to an outer edge of the lateral side and including an opening into an internal cavity.

2. The surgical buttress according to claim 1, wherein the body portion includes biocompatible and bioabsorbable materials.

3. The surgical buttress according to claim 1, further comprising a radioactive material disposed in at least some of the pockets.

4. The surgical buttress according to claim 1, wherein at least some of the pockets of the lateral sides contain a brachytherapy seed.

5. The surgical buttress according to claim 4, wherein the brachytherapy seed of each pocket includes isotopes selected from the group consisting of cesium and iodine.

6. The surgical buttress according to claim 1, wherein the pockets of each of the lateral sides are longitudinally aligned along the lateral side.

7. The surgical buttress according to claim 6, wherein the pockets of each of the lateral sides are disposed immediately adjacent one another.

8. The surgical buttress according to claim 1, wherein the surgical buttress has a fixed width defined by the distance between the outer edges of the lateral sides.

9. A method of embedding radioactive material into a surgical buttress, comprising:
   providing a surgical buttress having a body portion;
   providing a template holding a radioactive material;
   mating the template to the surgical buttress and creating pores in the body portion of the surgical buttress during mating of the template to the surgical buttress; and
   embedding the radioactive material into the pores of the body portion of the surgical buttress.

10. The method of claim 9, wherein the radioactive material is brachytherapy seeds, and embedding the radioactive material further includes embedding the brachytherapy seeds into the body portion of the surgical buttress.

11. The method of claim 10, wherein the brachytherapy seeds include at least one of iodine or cesium isotopes.

12. The method of claim 9, wherein embedding the radioactive material includes disposing the radioactive material on at least 10% of a surface area of the surgical buttress.

13. The method of claim 9, wherein embedding the radioactive material includes applying the radioactive material to at least one of lateral or outer sides of the surgical buttress.

14. A kit for performing surgical stapling, comprising:
   a surgical stapling instrument;
   at least one surgical buttress including a body portion and lateral sides extending from opposed edges of the body portion, each of the lateral sides defining pockets therein and each of the pockets having a width extending from the edge of the body portion to an outer edge of the lateral side and including an opening into an internal cavity; and
   a package of encapsulated radioactive material.

15. The kit of claim 14, wherein the surgical stapling instrument is a surgical stapling loading unit.

16. The kit of claim 15, wherein the loading unit is a removable and replaceable staple cartridge assembly.

17. The kit of claim 16, wherein the at least one surgical buttress is pre-loaded onto the surgical stapling instrument.

18. The kit of claim 14, wherein the lateral sides are wings that extend beyond sides of the surgical stapling instrument.

19. The kit of claim 14, wherein the encapsulated radioactive material is brachytherapy seeds.

20. The kit of claim 19, wherein the brachytherapy seeds have isotopes of cesium or iodine.

21. The kit of claim 14, wherein the package has shielding.

22. The kit of claim 14, wherein the package has a template and the encapsulated radioactive material is attached to the template.

* * * * *

UNITED STATES PATENT AND TRADEMARK OFFICE
CERTIFICATE OF CORRECTION

| | |
|---|---|
| PATENT NO. | : 10,293,553 B2 |
| APPLICATION NO. | : 14/699502 |
| DATED | : May 21, 2019 |
| INVENTOR(S) | : Racenet et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 762 days.

Signed and Sealed this
Nineteenth Day of May, 2020

Andrei Iancu
*Director of the United States Patent and Trademark Office*